(12) United States Patent
Bieniarz et al.

(10) Patent No.: US 7,642,064 B2
(45) Date of Patent: Jan. 5, 2010

(54) ENZYME-CATALYZED METAL DEPOSITION FOR THE ENHANCED DETECTION OF ANALYTES OF INTEREST

(75) Inventors: Christopher Bieniarz, Tucson, AZ (US); Michael Farrell, Tucson, AZ (US)

(73) Assignee: Ventana Medical Systems, Inc., Tucson, AZ (US)

( * ) Notice: Subject to any disclaimer, the term of this patent is extended or adjusted under 35 U.S.C. 154(b) by 718 days.

(21) Appl. No.: 11/015,646

(22) Filed: Dec. 20, 2004

(65) Prior Publication Data

US 2005/0100976 A1 May 12, 2005

Related U.S. Application Data

(63) Continuation-in-part of application No. 10/877,919, filed on Jun. 24, 2004.

(60) Provisional application No. 60/482,596, filed on Jun. 24, 2003.

(51) Int. Cl.
*C12Q 1/42* (2006.01)
*C12Q 1/44* (2006.01)
*C12Q 1/54* (2006.01)
*G01N 33/53* (2006.01)
*G01N 33/543* (2006.01)
*G01N 33/544* (2006.01)
*G01N 33/551* (2006.01)

(52) U.S. Cl. ............... 435/7.94; 435/7.1; 435/7.91; 435/14; 435/19; 435/21; 435/188; 436/503; 436/514; 436/518; 436/524; 436/528; 436/164

(58) Field of Classification Search ............... 435/7.1, 435/7.91, 7.94, 19, 21, 40.5, 14, 188; 436/503, 436/514, 518, 524, 528, 164
See application file for complete search history.

(56) References Cited

U.S. PATENT DOCUMENTS

| | | | |
|---|---|---|---|
| 5,073,483 A | 12/1991 | Lebacq | |
| 5,116,734 A | 5/1992 | Higgs et al. | |
| 5,143,854 A | 9/1992 | Pirrung et al. | |
| 5,252,743 A | 10/1993 | Barrett et al. | |
| 5,355,439 A | 10/1994 | Bernstein et al. | |
| 5,384,261 A | 1/1995 | Winkler et al. | |
| 5,412,087 A | 5/1995 | McGall et al. | |
| 5,424,186 A | 6/1995 | Fodor et al. | |
| 5,445,934 A | 8/1995 | Fodor et al. | |
| 5,451,683 A | 9/1995 | Barrett et al. | |
| 5,510,270 A | 4/1996 | Fodor et al. | |
| 5,571,639 A | 11/1996 | Hubbell et al. | |
| 5,595,707 A | 1/1997 | Copeland et al. | |
| 5,599,695 A | 2/1997 | Pease et al. | |
| 5,624,711 A | 4/1997 | Sundberg et al. | |
| 5,631,734 A | 5/1997 | Stern et al. | |
| 5,654,199 A | 8/1997 | Copeland et al. | |
| 5,677,195 A | 10/1997 | Winkler et al. | |
| 5,681,755 A * | 10/1997 | Noppe et al. | ................. 436/525 |
| 5,737,499 A | 4/1998 | Bernstein et al. | |
| 5,744,101 A | 4/1998 | Fodor et al. | |
| 5,981,185 A | 11/1999 | Matson et al. | |
| 6,083,726 A | 7/2000 | Mills, Jr. et al. | |
| 6,093,574 A | 7/2000 | Druyor-Sanchez et al. | |
| 6,156,501 A | 12/2000 | McGall et al. | |
| 6,180,351 B1 | 1/2001 | Cattell | |
| 6,203,989 B1 | 3/2001 | Goldberg et al. | |
| 6,225,077 B1 | 5/2001 | Schmidt et al. | |
| 6,296,809 B1 | 10/2001 | Richards et al. | |
| 6,576,424 B2 | 6/2003 | Fodor et al. | |
| 6,600,031 B1 | 7/2003 | Fodor et al. | |
| 6,670,113 B2 | 12/2003 | Hainfeld | |
| 2002/0142411 A1 | 10/2002 | Hainfeld | |

FOREIGN PATENT DOCUMENTS

| | | |
|---|---|---|
| WO | WO 90/15070 | 12/1990 |
| WO | WO 92/10092 | 6/1992 |
| WO | WO 93/09668 | 5/1993 |
| WO | WO 97/10365 | 3/1997 |
| WO | WO 03/035900 A1 | 5/2003 |

OTHER PUBLICATIONS

Nakamura et al., 1986. "Enzyme immunoassays: heterogeneous and homogeneous systems" in Handbook of Experimental Immunology (Weir et al., eds.) Blackwell,Scientific Publications, Oxford, pp. 27.1-27.20.*
Chee, M., et al., "Accessing Genetic Information with High-Density DNA Arrays," *Science* 274:610-614, The American Association for the Advancement of Science (1996).
"Gold and Silver Staining: Techniques in Molecular Morphology," Hacker, G.W. and Gu, J., eds., CRC Press, Boca Raton, FL, pp. 13-69 (Apr. 2002).
Merchenthaler, I., et al., "A Highly Sensitive One-step Method for Silver Intensification of the Nickel-Diaminobenzidine Endproduct of Peroxidase Reaction," *J. Histochem. Cytochem.* 37:1563-1565, The Histochemical Society, Inc. (1989).
Sia, S.K., et al., An Integrated Approach to a Portable and Low-Cost Immunoassay for Resource-Poor Settings, *Angew. Chem. Int. Ed.* 43:498-502, Wiley-VCH Verlag GmbH and Co. KGaA (Jan. 2004).
Sigma Technical Bulletin No. SE-1 (Jan. 1989), Silver Enhancer Kit, Product No. SE-100, pp. 1-6, Sigma Chemical Company (1989).

(Continued)

*Primary Examiner*—Ann Y Lam
*Assistant Examiner*—James L Grun
(74) *Attorney, Agent, or Firm*—Sterne, Kessler, Goldstein & Fox P.L.L.C.

(57) ABSTRACT

The invention is directed to enhanced methods for detecting an analyte of interest in situ, by immunoassay, or by hybridization comprising binding an enzyme-labeled conjugate molecule to an analyte of interest in the presence of a redox-inactive reductive species and a soluble metal ion. The enzyme catalyzes the conversion of the inactive reductive species to an active reducing agent, which in turn reduces the metal ion to a metal atom thereby providing an enhanced means of detecting the analyte via metal deposition.

14 Claims, 10 Drawing Sheets

OTHER PUBLICATIONS

Meur, S.K., et al., "A New Technique for Localization of Cellulose In Situ Using Silver Nitrate," *Stain Technol.* 58:97-100, The Williams & Wilkins Co. (1983).

Partanen, S., "A direct-colouring, metal precipitation method for the demonstration of arylsulphatases A and B," *Histochem. J.* 16:501-506, Chapman and Hall Ltd. (1984).

Patton, W.F., "Detection technologies in proteome analysis," *J. Chromatography B* 771:3-31, Elsevier Science B.V. (May 2002).

Azoulay, M., et al., "Prodrugs of anthracycline antibiotics suited for tumor-specific activation," *Anti-Cancer Drug Design* 10:441-450, Oxford University Press (1995).

Bagshawe, K.D., et al., "Antibody-directed enzyme prodrug therapy (ADEPT) for cancer," *Expert Opin. Biol. Ther.* 4:1777-1789, Ashley Publications Ltd. (2004).

Bakina, E. and Farquhar, D., "Intensely cytotoxic anthracycline prodrugs: galactosides," *Anti-Cancer Drug Design* 14:507-515, Oxford University Press (1999).

Bieniarz, C., et al., "Chromogenic Redox Assay for β-Lactamases Yielding Water-Insoluble Products: I. Kinetic Behavior and Redox Chemistry," *Analytical Biochemistry* 207:321-328, Academic Press, Inc. (1992).

Bieniarz, C., et al., "Chromogenic Redox Assay for β-Lactamases Yielding Water-Insoluble Products: II. Heterogeneous Sandwich Assay for hCG," *Analytical Biochemistry* 207:329-334, Academic Press, Inc. (1992).

Cheng, H., et al., "Synthesis and Enzyme-Specific Activation of Carbohydrate-Geldanamycin Conjugates with Potent Anticancer Activity," *J. Med. Chem.* 48:645-652, American Chemical Society (2005).

Farquhar, D., et al., "Suicide gene therapy using *E. coli* β-galactosidase," *Cancer Chemother Pharmacol* 50:65-70, Springer-Verlag (2002).

Fujimoto, Z., et al., "Crystal Structure of Rice α-Galactosidase Complexed with D-Galactose," *The Journal of Biological Chemistry* 278:20313-20318, The American Society for Biochemistry and Molecular Biology, Inc. (2003).

Han, H.-K. and Amidon, G.L., "Targeted Prodrug Design to Optimize Drug Delivery," *AAPS Pharmsci* 2:1-11, article 6, American Association of Pharmaceutical Scientists (2000).

Harding, F.A., et al., "A α-lactamase with reduced immunogenicity for the targeted delivery of chemotherapeutics using antibody-directed enzyme prodrug therapy," *Mol Cancer Ther* 4:1791-1800, American Association for Cancer Research (2005).

Hult, K. and Berglund, P., "Enzyme promiscuity: mechanism and applications," *Trends in Biotechnology* 25: 231-238, Elsevier Science Ltd. (2007).

Isorna, P., et al., "Crystal Structures of *Paenibacillus polymyxa* β-Glucosidase B Complexes Reveal the Molecular Basis of Substrate Specificity and Give New Insights into the Catalytic Machinery of Family I Glycosidases," *J. Mol. Biol.* 371:1204-1218, Elsevier Science Ltd. (2007).

Niculescu-Duvaz, I. and Springer, C.J., "Antibody-directed enzyme prodrug therapy (ADEPT): a review," *Advanced Drug Delivery Reviews* 26:151-172, Elsevier Science Ltd. (1997).

Rooseboom, M., et al., "Enzyme-Catalyzed Activation of Anticancer Prodrugs," *Pharmacol Rev* 56:53-102, The American Society for Pharmacology and Experimental Therapeutics (2004).

Sanz-Aparicio, J., et al., "Crystal Structure of β-Glucosidase A from *Bacillus polymyxa*: Insights into the Catalytic Activity in Family 1 Glycosyl Hydrolases," *J. Mol. Biol.* 275:491-502, Academic Press, Ltd. (1998).

Senter, P.D. and Springer, C.J., "Selective activation of anticancer prodrugs by monoclonal antibody-enzyme conjugates," *Advanced Drug Delivery Reviews* 53:247-264, Elsevier Science B.V. (2001).

Smyth, T.P., et al., "Extending the β-Lactamase-Dependent Prodrug Armory: S-Aminosulfeniminocephalosporins as Dual-Release Prodrugs," *J. Org. Chem.* 64:3132-3138, American Chemical Society (1999).

Xu, G. and McLeod, H.L., "Strategies for Enzyme/Prodrug Cancer Therapy," *Clinical Cancer Research* 7:3314-3324, American Association for Cancer Research (2001).

\* cited by examiner

Ascorbic acid-2-phosphate (AAP)

Sesamol phosphate (SP)

Hydroquinone-1,4-diphosphate (HQP)

2,2,5,7,8-Pentamethyl-6-chromanol phosphate (PMCP)

ENZYME-CATALYZED METAL DEPOSITION FOR THE ENHANCED DETECTION OF ANALYTES OF INTEREST

CROSS REFERENCE TO RELATED APPLICATIONS

This application is a continuation-in-part of U.S. application Ser. No. 10/877,919, filed Jun. 24, 2004, which claims the benefit of U.S. Provisional Appl. No. 60/482,596, filed Jun. 24, 2003, the contents of which are hereby incorporated by reference in their entireties.

BACKGROUND OF THE INVENTION

1. Field of the Invention

The present invention relates generally to the field of chemistry, and in particular, immunochemistry. More specifically, the present invention relates to a method for the enhanced detection of an analyte by using an enzyme-catalyzed reaction for the localized deposition of metal atoms. The present method of detection can be employed in various types of assays, such as, e.g., in-situ histochemical, immunoassays such as ELISA, and hybridization to nucleic acid microarrays.

2. Related Art

Tissue staining is an ancient art by modern standards that goes back over one hundred years. Recently, efforts have been made to automate the procedure of applying different types of chemical and biochemical stains to tissue sections. Instruments that have been invented for this purpose include the Ventana Medical Instruments' line of dual carousel-based instruments such as the 320, ES®, NexES®, BENCH-MARK®, and the BENCHMARK® XT. Patents that describe these systems include U.S. Pat. Nos. 5,595,707, 5,654,199, 6,093,574, and 6,296,809, all of which are incorporated herein by reference in their entirety. Another type of automated stainer is the TechMate® line of stainers, described in U.S. Pat. Nos. 5,355,439 and 5,737,499, both of which are incorporated herein by reference in their entireties.

Over the years, various manual detection methods have been used in the field of histochemistry. Generally, once a molecular marker or target of interest in a tissue sample has been identified through biomolecular studies, it needs to be rendered visible under the light microscope for a pathologist or other medical specialist to interpret. The first detection step involves the use of an anti-target primary antibody detectably labeled with biotin, digoxigenin, fluorescein or other haptens to locate the biological target of interest. Next, an anti-hapten secondary antibody conjugated to an enzyme or other reporter molecule is used to locate the primary antibody. Typically used enzymes are well-known to those of ordinary skill in the art, and include horseradish peroxidase ("HRP") or alkaline phosphatase ("AP"). These enzymes then catalyze the precipitation of a chromogenic substrate in the immediate vicinity of the primary-secondary antibody complex. Chromogens such as nitro blue tetrazolium (NBT/BCIP), 3,3'-diaminobenzidine tetrahydrochloride (DAB), and 3-amino-9-ethylcarbazole (AEC) are well-known. Alternately, enzyme substrate interactions may produce chemiluminescent signals, which can be captured on photographic film.

Other labels that have been used for histochemical detection include: $^{125}$I-labeling of the secondary antibody, which can be detected using a photographic film; fluorescein isothiocyanate-labeled second antibody, which can be detected using UV light; $^{125}$I-labeled Protein A, which can be used instead of a secondary antibody, as it will bind to the Fc region of IgG molecules; gold-labeled secondary antibody, which is directly visible as a red color when it is bound with the secondary antibody to the primary antibody; biotinylated secondary antibody, which when incubated with the secondary antibody, then incubated with enzyme-conjugated avidin or streptavidin ("SA") which binds strongly to the biotin, will give an enhanced signal, as multiple biotin molecules can be attached to a single antibody molecule. Enzymes typically used include AP or HRP.

Enzyme immunoassays (EIA), such as, for example, enzyme-linked immunosorbant assays (ELISAs) are widely used for the determination, either qualitative or, mostly, quantitative, of a nearly unlimited variety of organic substances, either of natural origin or synthetic chemical compounds, such as peptides, proteins, enzymes, hormones, vitamins, drugs, carbohydrates, etc., for various purposes, such as, e.g., diagnostic, forensic, pharmacologic, and food quality control.

Many different variants of ELISA methods exist that are familiar to those of ordinary skill in the art. In a classical "sandwich" ELISA, to detect the presence or measure the concentration of an analyte (i.e., antigen) of interest such as tumor markers, hormones and serum proteins in a biological sample (e.g., blood, plasma, serum, urine, saliva, sputum), the sample is incubated on a solid support (e.g., microtiter well) that has been precoated with a first binding partner for the analyte (a.k.a. "primary antibody" or "capture antibody"). The sample and the primary antibody are incubated for a sufficient time to permit binding between the antibody and the antigen in the sample.

As a result of this first reaction, any analyte present in the sample will have become bound to its binding partner and thereby to the solid support. After the solid support has been washed, steps are taken to make the result detectable. The solid support having attached thereto the binding partner and analyte, if any, is contacted with a second binding partner for the analyte (a.k.a. the "secondary antibody"). In most cases, the secondary antibody carries a label/marker allowing its detection by generation of a chromogenic, fluorogenic, or other type of signal. In this type of assay, the antigen is "sandwiched" in between the primary and the labeled secondary antibody.

Typically, in ELISA-type assays, the label consists of an enzyme capable of a detectable conversion of a substrate, e.g., horseradish peroxidase is capable of converting, in the presence of hydrogen peroxide, a substrate, such as 3, 3', 5,5'-tetramethylbenzidine, into a colored product. Normally, after the enzyme-labeled reactant has been attached to the immobilized complex, the solid phase with complex bound thereto is washed before the actual detection phase is entered.

In the detection phase, substrate solution is added to the solid phase with attached complex and the conversion, if any, of the substrate is detected. To allow quantitative measurement of the analyte, the solid phase is incubated with the substrate solution for a fixed time, which should be sufficiently long to allow a substantial enzymatic conversion of the substrate into a colored substance. After termination of the substrate-converting reaction, the intensity of the coloration, which is proportional to the immobilized amount of enzyme, is measured by optical means, such as a photometer to measure the absorbance at a chosen wavelength, such as 450 nm.

A disadvantage of the existing ELISA techniques, however, is that the adsorption and detection phases, to secure assay sensitivity, can be very time consuming for samples having low analyte concentrations. In such samples, the rate of adsorption of analyte to the surface is proportional to the concentration of analyte in the solution, and thus will also become very low, even in well-stirred systems. To allow a reliable measurement of analytes present in a liquid at a concentration on the order of nanograms or even picograms per ml, the adsorption phase may require a reaction time of one to several hours.

The most sensitive of such sandwich-type ELISA assays are capable of detecting 1 amol ($1\times10^{-18}$ M) of analyte. However, in the sandwich type ELISA, the analyte must have at least two antigenic sites that can be recognized simultaneously by the primary and secondary antibodies (or binding partners). Accordingly, such sandwich assays cannot be used for the detection of small peptides, most drugs, or synthetic drug candidates.

Competitive ELISA is another type of ELISA methodology that is used to detect or quantify analytes such as small molecule antigens (i.e., T3, T4, progesterone, etc.). In competitive ELISA, a carefully titrated concentration of analyte-specific antibody is coated onto the inside wall of the microwell. In a single reaction, antigen from the test sample and the enzyme-labeled antigen conjugate compete for a limited number of immobilized antibody-binding sites. The amount of antibody-antigen-enzyme complex bound to the solid phase (microwell) is inversely proportional to the amount of antigen present in the sample.

An expanding area of polynucleotide analysis is DNA array technology. This technology uses arrays of nucleic acid probes, such as oligonucleotides, to detect complementary nucleic acid sequences in a sample nucleic acid of interest (the "target" nucleic acid). For example, an array of nucleic acid probes is fabricated at known locations on a substrate such as a chip or glass slide. A labeled nucleic acid is then brought into contact with the chip and a scanner generates an image file indicating the locations where the labeled nucleic acids are bound to the chip. Based upon the image file and identities of the probes at specific locations, it becomes possible to extract information such as the expression pattern of a nucleic acid of interest (see, e.g., U.S. Pat. No. 6,225,077).

Methods using arrays of nucleic acids immobilized on a solid substrate are disclosed, for example, in U.S. Pat. No. 5,510,270. In this method, an array of diverse nucleic acids is formed on a substrate. The fabrication of arrays of polymers, such as nucleic acids, on a solid substrate, and methods of use of the arrays in different assays, are described in: U.S. Pat. Nos. 6,600,031, 6,576,424, 6,203,989, 6,180,351, 6,156,501, 6,083,726, 5,981,185, 5,744,101, 5,677,195, 5,624,711, 5,599,695, 5,445,934, 5,384,261, 5,571,639, 5,451,683, 5,424,186, 5,412,087, 5,384,261, 5,252,743 and 5,143,854; PCT WO 92/10092; PCT WO 93/09668; PCT WO 97/10365, which are incorporated by reference in their entireties.

Accessing genetic information using high density DNA arrays is further described in Chee, *Science* 274:610-614 (1996). The combination of photolithographic and fabrication techniques allows each probe sequence to occupy a very small site on the support. The site may be as small as a few microns or even a small molecule. Such probe arrays may be of the type known as Very Large Scale Immobilized Polymer Synthesis (VLSIPS™). U.S. Pat. Nos. 5,631,734 and 5,143,854 and PCT patent publication Nos. WO 90/15070 and 92/10092.

Typically, the existence of a nucleic acid of interest in array technology and other DNA detection methods is indicated by the presence or absence of an observable "label" attached to a probe or attached to amplified sample DNA.

Clearly, whether one is detecting and/or quantifying analytes of interest in in situ histochemical assays, immunoassays, such as ELISA, or hybridization assays to arrays or microarrays of nucleic acids, detecting the signal formed by the particular enzymatic reaction sensitively, rapidly, and then being able to accurately relate it to the amount of analyte in a biological sample, is of paramount importance.

Metallographic detection of analytes is well-known to those skilled in the arts of pathology, microscopy, and medical morphology. See, e.g., "Gold and Silver Staining: Techniques in Molecular Morphology", edited by Gerhard W. Hacker and Jiang Gu, CRC Press, Boca Raton, Fla. (2002).

Metallic enhancement of immunohistochemical detection is taught in U.S. Pat. No. 5,116,734 (Higgs et al.), incorporated herein by reference in its entirety. The '734 patent is directed to a composition of matter and a process for detecting the presence of an oxidative catalyst in a biological sample. The composition comprises a precipitate formed by oxidation of a chromogenic substrate in the presence of the catalyst, together with two or more co-precipitated reduced metals. A strong signal is formed with which to detect an oxidation catalyst which is localized to a target molecule. Target molecules may be nucleic acids, antibodies, or cell surface antigens. In particular, Higgs et al. rely on a chromogenic precipitate and two or more metals, for the purpose of detecting an oxidative catalyst.

Merchanthaler et al., *J. Histoch. And Cytochem.*, 37:1563-1565 (1989) teach silver intensification of the oxidatively polymerized chromogen DAB by pre-treating the DAB with nickel ions.

A more recent example of metallic enhancement of immunohistochemical detection includes U.S. Pat. No. 6,670,113 (Hainfeld). The '113 patent is directed to a method of producing metal in a zero oxidation state from metal ions, comprising: providing metal ions of at least one metal selected from cesium, periodic table group 1b, 2a, 4a and 8, an oxygen containing oxidizing agent and a reducing agent selected from at least one of hydroquinone, a hydroquinone derivative or n-propyl gallate; providing an oxido-reductase enzyme; combining the enzyme with the metal ions, oxidizing agent and reducing agent; and reducing at least some of the metal ions to metal in a zero oxidation state. In particular, silver ion reduction to silver metal in proximity to horseradish peroxidase when exposed to hydrogen peroxide and hydroquinone is taught.

There continues to be a need in the art for better and more sensitive biochemical techniques for detecting analytes of interest in various assay settings. For example, there is a need for improved methods of detecting immunohistochemical epitopes and DNA targets of interest via bright field light microscopy. There continues to be a need for more sensitive and improved methods for detecting and quantifying analytes of interest, such as antigens, cells, hormones, drugs, or any biologically active molecule, using enzyme immunoassays and more particularly, ELISA-based assays. Finally, there is a need in the art for better techniques for rapidly and sensitively detecting hybridization to arrays or microarrays of nucleic acids on solid supports.

SUMMARY OF THE INVENTION

In the present invention, regardless of assay employed, the detection and quantification of the biological analyte of interest is based on a metal precipitate forming system that is catalyzed by an enzyme, such as, e.g., alkaline phosphatase. The enzyme catalyzes the dephosphorylation of a reducing agent precursor into an active reducing agent, which in turn reduces a metal ion into a detectable and quantifiable metal precipitate. By using the methods of the invention, low concentrations of analyte in assays such as in situ histochemical assays, immunoassays such as ELISA, or hybridization to DNA microarrays on glass slides, can be determined accurately, rapidly, and with high assay sensitivity.

The present invention provides methods of detecting in situ an immunohistochemical epitope or nucleic acid sequence of interest in a biological sample comprising binding an enzyme-labeled conjugate molecule to the epitope or sequence of interest in the presence of a redox-inactive reductive species and a soluble metal ion, thereby catalyzing the reduction of the metal ion to a metal in oxidation state 0, at or about the point where the enzyme is anchored.

The present invention also provides novel compositions of matter, which may be used in the claimed methods. Novel phosphate derivatives of reducing agents are described that when exposed to a phosphatase enzyme are activated to their reducing form, thereby reducing metal ions to insoluble metal particles in oxidation state 0.

In one embodiment, the present invention provides a compound having the general structure (IV) shown below:

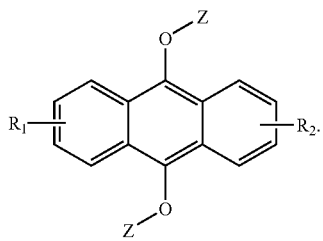

IV wherein
$R_1$ may be H, alkyl, aryl, carboxyl, carboxyalkyl, $NH_2$, $(CH_2)_n$—COOH—, nitro, ether, thioether and sulphonate;
$R_2$ may be H, alkyl, aryl, carboxyl, carboxyalkyl, $NH_2$, or $(CH_2)_n$—COOH—, nitro, ether, thioether and sulphonate; and
Z may be $PO_3^{2-}$, H, α-galactose, β-galactose, α-glucose, β-glucose, ester, and β-lactam; but both Zs may not be H. A preferred compound has both Zs=phosphate.

In another embodiment, the present invention is directed to a compound having the general structure (V):

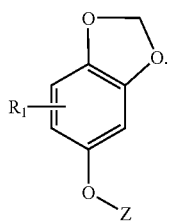

V wherein
$R_1$ may be H, alkyl, aryl, carboxyl, carboxyalkyl, $NH_2$, $(CH_2)_n$—COOH—nitro, ether, thioether and sulphonate; and
Z may be $PO_3^{2-}$, α-galactose, β-galactose, α-glucose, β-glucose, ester, and β-lactam. A particularly preferred compound has Z=phosphate.

In yet another embodiment, the present invention is directed to a compound having the general structure (VI):

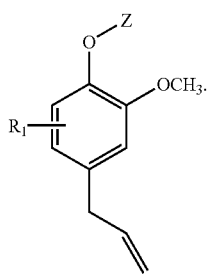

VI wherein
$R_1$ may be H, alkyl, aryl, carboxyl, carboxyalkyl, $NH_2$, $(CH_2)_n$—COOH—nitro, ether, thioether or sulphonate; and
Z may be $PO_3^{2-}$, α-galactose, β-galactose, α-glucose, β-glucose, ester, and β-lactam. A particularly preferred compound has Z=phosphate.

In yet another embodiment, the present invention is directed to a compound having the general formula (VII):

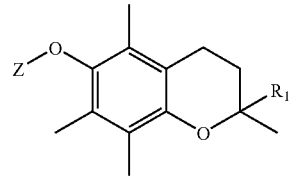

VII wherein
$R_1$ may be H, alkyl, aryl, carboxyl, carboxyalkyl, NH2, $(CH_2)_n$—COOH—nitro, ether, thioether and sulphonate; and
Z may be $PO_3^{2-}$, β-galactose, β-galactose, α-glucose, β-glucose, ester, and β-lactam. Two particularly preferred compounds have $R_1$=methyl or $CH_2$—$(CH_2$—$CH_2$—CH $(CH_3)$—$CH_2)_3$—H, and Z=phosphate.

The present invention also provides a method of in situ staining a biological sample having an epitope or nucleotide sequence of interest, comprising the steps of:
(a) contacting said biological sample with a conjugate molecule having a hapten; (b) contacting said hapten with a hapten-binding partner conjugated to a label enzyme; and (c) contacting said biological sample with a redox-inactive reductive species that is a substrate for said label enzyme in the presence of a metal ion.

The present invention also provides a method of in situ staining a biological sample having an epitope or nucleotide sequence of interest, comprising the steps of:
(a) contacting said biological sample with a biotinylated primary antibody; (b) contacting said biological sample having said biotinylated primary antibody bound to it with a streptavidin-alkaline phosphatase conjugate; and (c) contacting said biological sample of step (b) with ascorbic acid phosphate in the presence of silver ion at a pH greater than 7. An optional gold ion pretreatment step may also be applied in order to enhance the silver deposition.

The present invention also provides a method for detecting and quantifying an analyte of interest in a biological sample using an enzyme immunoassay, such as an ELISA-based assay, by measuring enzyme-catalyzed metal precipitate formation on the surface of the solid support. More specifically, the method comprises the steps of: (a) contacting a biological sample containing an analyte of interest with a primary antibody immobilized on a solid support, such that the presence of the analyte in the biological sample will result in the formation of a primary antibody-analyte complex; (b) contacting said complex of step (a) with a secondary antibody conjugated to a label enzyme, such that the presence of analyte in the biological sample will result in a primary antibody-analyte-secondary antibody complex; (c) contacting the complex formed in step (b) with a redox inactive reductive species in the presence of metal ion so that a metal precipitate will form on the solid support following reduction; (d) enhancing said metal precipitate; and (e) detecting and quantifying the amount of analyte in the sample by measuring the amount of metal precipitate formed on the solid support.

A particularly preferred enzyme label is alkaline phosphatase, a particularly preferred redox inactive reductive species is ascorbic acid phosphate, and a particularly preferred metal ion is silver ion. An optional gold ion pretreatment step may also be applied to enhance the silver deposition. In the embodiment where the enzyme label is alkaline phosphatase, the optimal pH is between 7 and 10.5, preferably 8-9, and most preferably 9.

The present invention also provides a method for detecting nucleic acid sequences following hybridization to nucleic acid microarrays by measuring enzyme-catalyzed metal precipitate formation on the surface of the solid support immobilizing the nucleic acid. More specifically, the method comprises the steps of: (a) labeling DNA isolated from a biological sample with a first member of a specific binding pair; (b) hybridizing said DNA of step (a) to a microarray of nucleic acid sequences immobilized on a solid support under appropriate hybridization conditions; (c) incubating said microarray of step (b) with a label enzyme conjugated to a second member of said specific binding pair; (d) incubating said microarray with a redox inactive reductive species in the presence of metal ion so that a metal precipitate will form on the microarray following reduction; (e) enhancing said metal precipitate; and (f) detecting nucleic acid sequences that are complementary to at least one of the microarray of nucleic acid sequences immobilized on the solid support by visualizing the metal precipitate formed on the solid support.

The present invention also provides kits for carrying out the claimed methods conveniently.

In any of the methods or kits of the invention, the detection and quantification of the biological analyte of interest is based on a metal precipitate forming system that is catalyzed by an enzyme, such as, e.g., alkaline phosphatase. The enzyme catalyzes the dephosphorylation of a redox inactive reductive species into an active reducing agent, which in turn reduces metal ion into a detectable and quantifiable metal precipitate.

By using the methods of the invention, low concentrations of analyte in either an in situ histochemical assay, an immunoassay, such as ELISA, or following nucleic acid hybridization to ordered DNA microarrays on a glass slide, can be determined rapidly. Thus, the present invention results in a large increase in assay sensitivity in shorter assay times.

DETAILED DESCRIPTION OF THE INVENTION

The present invention is directed to methods of detecting an analyte of interest by using enzyme-catalyzed metal deposition. The methods may be used for detecting analytes of interest in various assays, such as, e.g., in situ histochemical assays, immunoassays such as ELISA, or by DNA microarray technology. The present invention is also directed to kits for conveniently carrying out said methods.

Figure 12:
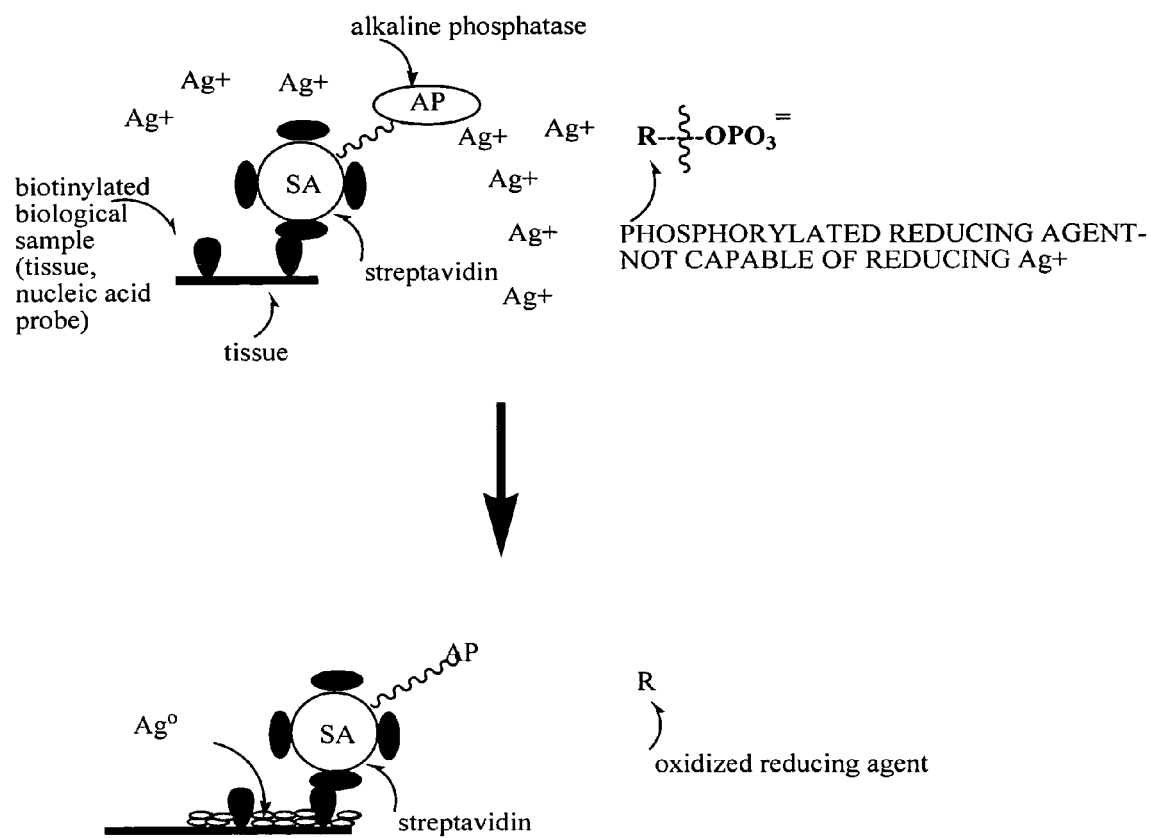
FIG. 12 is a schematic representation of an embodiment of the invention, whereby enzyme-catalyzed metal deposition is used for the enhanced in situ detection of immunohistochemical epitopes and nucleic acid sequences. Briefly, alkaline phosphatase ("AP") conjugated streptavidin ("SA"), upon binding to the biotinylated epitope or nucleic acid probe in the tissue, catalyzes the cleavage of the phosphorylated-reducing agent (a.k.a. "the redox-inactive reductive species"). The phosphorylated reducing agent, i.e., hydroquinone bis-phosphate, ascorbate phosphate etc. is unable to reduce silver when phosphorylated. Upon release of the reducing agent as a result of the action of the AP, the reducing agent "R" reduces Ag$^+$ to Ag$^o$. The precipitated silver is developed under appropriate conditions and detected by bright field microscopy.
Figure 13:
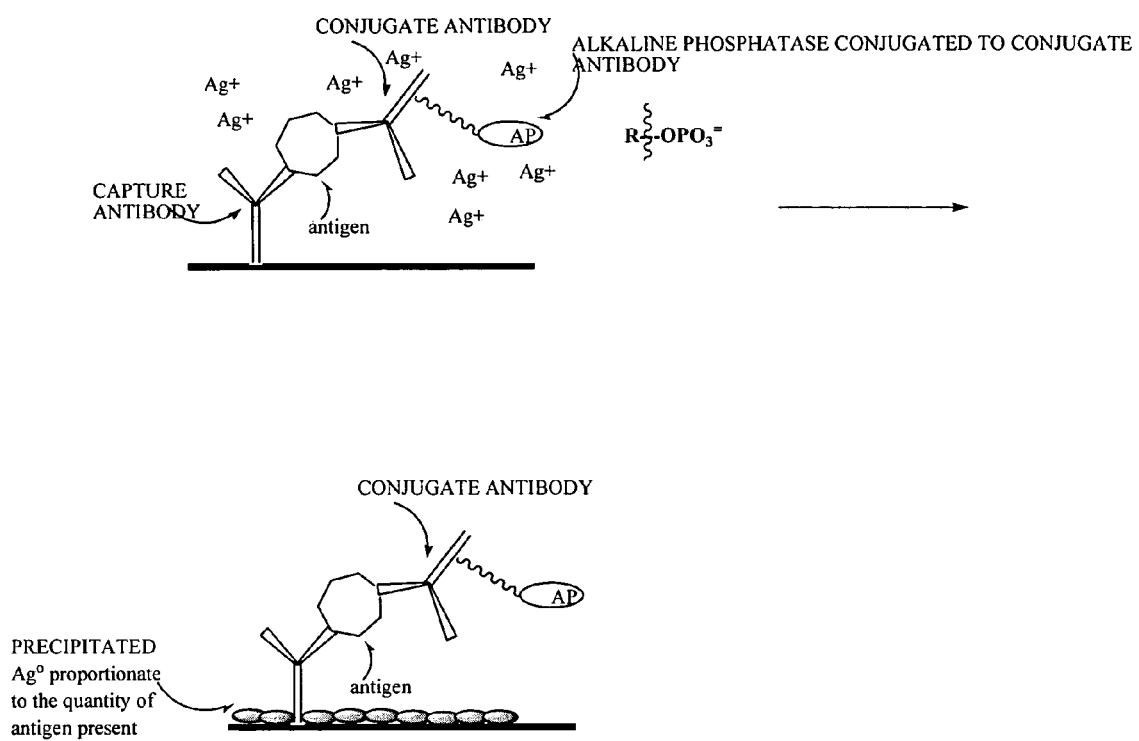
FIG. 13 is a schematic representation of an embodiment of the invention, whereby enzyme-catalyzed metal deposition is used for the enhanced detection of analytes in an ELISA-based assay. Briefly, the capture antibody, immobilized on the surface of a microtiter plate or any other suitable solid support, is first incubated with an antigen, i.e., virus, virus fragment, bacterial protein, glycolipid, receptor, etc. The surface and the adhering half-sandwich are washed with a suitable buffer. The conjugate antibody consisting of antibody-alkaline phosphatase enzyme, said antibody directed against the antigen is added and the sandwich is washed again. Silver ions are added at pH of 7-10.5 followed immediately by the phosphorylated reducing agent. After hydrolysis of the phosphate and unmasking of the active reducing agent, the silver ion is deposited on the surface of the microtiter plate.

In one embodiment, the present invention is directed to a method of detecting an immunohistochemical epitope or nucleic acid sequence of interest by first binding a conjugate molecule to the epitope or sequence of interest. The conjugate molecule is labeled with an enzyme which catalyzes the transformation of a redox-inactive reductive species into an active reducing agent, thereby allowing the reduction of a chromogenically detectable metal at or about the point where the enzyme is anchored. More specifically, the method of the invention relies on a novel method of using alkaline phosphatase or other enzymes, i.e., glucosidases, esterases, β-galactosidases, and β-lactamase, as labels capable of catalyzing the dephosphorylation of a redox-inactive enzyme substrate(s), i.e., ascorbic acid phosphate, which after enzyme-catalyzed dephosphorylation becomes an extremely efficient reducing agent capable of reducing silver and/or gold ions to metallic silver and/or gold atoms. Since the reduction occurs near or at the epitope or nucleotide sequence of interest, the precipitated metallic silver/gold in oxidation state 0 accumulates in the vicinity of the epitope or nucleic acid sequence greatly enhancing the visual detectability of the epitope in microscopic diagnostic procedures. A schematic representation of this first embodiment may be found in FIG. 12.

In a second embodiment, the present invention provides a method for detecting and quantifying an analyte of interest in an enzyme immunoassay, such as an ELISA-based assay, by measuring enzyme-catalyzed metal precipitate formation on the surface of the solid support. More specifically, the method comprises the steps of: (a) contacting a biological sample containing an analyte of interest with a primary antibody immobilized on a solid support, such that the presence of the analyte in the biological sample will result in the formation of a primary antibody-analyte complex; (b) contacting said complex of step (a) with a secondary antibody conjugated to a label enzyme, such that the presence of analyte in the biological sample will result in a primary antibody-analyte-secondary antibody complex; (c) contacting the complex formed in step (b) with a redox inactive reductive species in the presence of metal ion so that a metal precipitate will form on the solid support following reduction; (d) enhancing said metal precipitate; and (e) detecting and quantifying the amount of analyte in the sample by measuring the amount of metal precipitate formed on the solid support.

In a third embodiment, the present invention also provides a method for detecting nucleic acids following hybridization to nucleic acid microarrays by measuring enzyme-catalyzed metal precipitate formation on the surface of the solid support immobilizing the nucleic acid. More specifically, the method comprises the steps of: (a) labeling DNA isolated from a biological sample with a first member of a specific binding pair; (b) hybridizing said DNA of step (a) to a microarray of nucleic acid sequences immobilized on a solid support under appropriate hybridization conditions; (c) incubating said microarray of step (b) with a label enzyme conjugated to a second member of said specific binding pair; (d) incubating said microarray with a redox inactive reductive species in the presence of metal ion so that a metal precipitate will form on the microarray following reduction; (e) enhancing said metal precipitate; and (f) detecting nucleic acid sequences that are complementary to at least one of the microarray of nucleic acid sequences immobilized on the solid support by visualizing the metal precipitate formed on the solid support.

The present invention also provides kits for carrying out the disclosed methods conveniently. A kit for detecting an analyte of interest in a biological sample is described. The kit comprises one or more containers, each container adapted to hold a specific binding member for the analyte of interest, a redox-inactive reductive species, an enzyme label for rendering said reductive species active, a metal ion, and reagents for metal enhancement. In some embodiments, said specific binding member is immobilized on a solid support.

In a preferred embodiment, the metal ion in the kit is silver ion and the reagents for metal enhancement are reagents for silver enhancement, such as those found in Sigma's Silver Enhancer Kit (Sigma Chemical Company, Product No. SE-100, ST. Louis, Mo.).

The terms used herein are well-known to persons of ordinary skill in the art. Nevertheless, to provide a clear and consistent understanding of the specification and claims and the scope given to such terms, the following definitions are provided:

As used herein, the term "analyte" means any biological substance for which there exists a naturally occurring specific binding member or for which a specific binding member can be prepared. The analyte is assayable by means known to those skilled in the art, such as, e.g., ELISA. The analyte may be, for example, proteins, peptides, antigens (viral, viral fragment, bacterial, receptor, glycolipid), haptens, antibodies (monoclonal or polyclonal), immunohistochemical epitopes, nucleic acid sequences, cells, enzymes, hormones, vitamins, steroids, drugs, carbohydrates, and so on.

The public accessibility of or details for the preparation of such antibodies and the suitability for use as specific binding members are well-known to those skilled in the art. Viruses which can be tested include hepatitis-causing viruses (for example, hepatitis A viruses, hepatitis B viruses, hepatitis C viruses, hepatitis delta, and hepatitis E viruses), human immunodeficiency viruses (such as HIV-1, HIV-2), the HTLV-I and HTLV-II viruses, and the like.

As used herein, a "specific binding member" is one member of a "specific binding pair." A "specific binding pair" refers to two different molecules where one of the molecules, through chemical or physical means, specifically binds to the second molecule. Therefore, in addition to antigen and antibody specific binding pairs of common immunoassays, other specific binding pairs include biotin and avidin/streptavidin, carbohydrates and lectins, complementary nucleotide sequences, effector and receptor molecules, cofactors and enzymes, enzyme inhibitors and enzymes, and the like. Furthermore, specific binding pairs can include members that are analogs of the original specific binding members, for example, an analyte-analog. Immunoreactive specific binding members include antigens, antigen fragments, antibodies and antibody fragments, both monoclonal and polyclonal, and complexes thereof, including those formed by recombinant DNA molecules.

As used herein, the term "hapten," refers to small, single epitope molecules which are capable of binding to an antibody.

As used herein, the term "conjugate" means any chemically or covalently crosslinked cluster of molecules. Examples of "conjugates" include antibody covalently bound ("conjugated") to an enzyme or biotin and DNA chemically bound to a chromogen.

As used herein, the term "complex" means any non-covalently bound molecule formed by the combination of two or more molecules. Examples of "complexes" include antibody-antigen interactions, DNA-cDNA, and avidin/streptavidin-biotin. Any of the specific binding pairs mentioned above form complexes upon binding.

The proteins streptavidin and avidin have a natural affinity for biotin. Biotin is used pervasively throughout the anatomical pathology laboratory as streptavidin/avidin's binding partner. Almost all commercially available primary antibodies are labeled with biotin so that streptavidin/avidin conjugates can be used to localize the primary antibody. In one aspect of the present invention, the biotin-streptavidin binding motif is used to co-localize streptavidin with AP. Secondary antibodies labeled with biotin are targeted to the binding site in the tissue, and the streptavidin-AP conjugate brings the AP into the same location through streptavidin's binding to biotin.

The term "biological sample," includes samples which can be tested by the methods and kits of the present invention described herein and include human and animal body fluids such as whole blood, serum, plasma, cerebrospinal fluid, urine, lymph fluids, and various external secretions of the respiratory, intestinal and genitourinary tracts, tears, saliva, milk, white blood cells, myelomas and the like, biological fluids such as cell culture supernatants, fixed tissue specimens and fixed cell specimens. Any substance which can be diluted and tested with recombinant proteins and assay formats described in the present invention are contemplated to be within the scope of the present invention.

Numerous assay formats are known in the art, and all are considered to be within the scope of the invention, so long as the specific binding member is capable of being labeled with an enzyme that catalyzes the dephosphorylation of a phosphorylated reducing agent to an active one, and subsequently the reduction of a metal ion to a metal atom. Thus, immunohistochemical assays, one and two-step sandwich immunoassays, hemagglutination assays, competitive assays, neutralization assays, immunodot assays, and hybridization assays to nucleic acid arrays and microarrays are all considered within the scope of the present invention.

As used herein, the term "detecting in situ" means to be able to visualize the biological feature of interest in tissue or intact cellular specimens. Tissue is, for example, fixed, paraffin-embedded 4-8 µm-thick tissue sections such as are commonly mounted on glass microscope slides and then prepared and stained for immunohistochemistry, or in situ hybridization using oligonucleotide probes. Intact cells include cytospins, ThinPreps™ (Cytyc, Inc., Boxborough, Mass.) and other methods of preparing intact cells for staining. In situ can also refer to tissue arrays mounted on glass microscope slides.

As used herein, the term "chromogen" means an enzyme substrate that yields a detectable reaction product that is usually colored. Examples of typical chromogens include Nuclear Fast Red, nitro blue tetrazolium (NBT/BCIP), 3,3'-diaminobenzidine tetrahydrochloride (DAB), and 3-amino-9-ethylcarbazole (AEC). Many more chromogens are known to those skilled in the art and are available through suppliers such as Pierce Chemical (Rockford, Ill.).

As used herein, the term "kit" means a packaged combination of one or more vessels, containers, devices or the like holding the necessary reagents for detecting an analyte of interest. The kit is appended with written or computerized instructions for performing the method. The kit may contain an AP-labeled antibody, nucleic acid, ligand, or the like. The kit for detecting an analyte of interest in a biological sample comprises one or more containers, each container adapted to hold a specific binding member for the analyte of interest, a redox-inactive reductive species, an enzyme label for rendering said reductive species active, a metal ion, and reagents for metal enhancement. In some embodiments, said specific binding member is immobilized on a solid support.

As used herein, the term "solid support" is intended to mean any suitable solid support known to those skilled in the art, and includes, for example, microtiter plates, glass slides or beads, test tubes, polystyrene beads, magnetic beads, chromatographic membranes, membrane strips made of synthetic or natural materials, such as polystyrene, nylon, nitrocellulose membrane, or filter paper, dipsticks, microparticles, latex particles, chips, or silica strips (Affymetrix, Santa Clara, Calif.). Suitable methods for immobilizing peptides on solid phases include ionic, hydrophobic, covalent interactions and the like.

As used herein, the term "label enzyme" means an enzyme that catalyzes the creation of a redox-active reductive species (a.k.a. "reducing agent") from a redox-inactive reductive precursor species. The label enzyme may be alkaline phosphatase or other enzyme conjugated to an antibody, nucleic acid, or conjugate protein such as streptavidin. Although alkaline phosphatase is a particularly preferred label enzyme, other enzymes that can be used in the methods and kits of the invention include acid phosphatase, alpha- and beta-galactosidases, alpha- and beta-glucosidases, esterases generally, and beta-lactamases, specifically cephalosporinases and penicillinases.

One skilled in the art will be knowledgeable of the optimal pH for a given enzyme. Generally, however, when the enzyme label used is alkaline phosphatase, the deprotection of the phosphate groups on the enzyme substrate should optimally be done at a pH between 7-10.5, preferably 8-9, and most preferably 9. When the enzyme label used is acid phosphatase, however, the deprotection of the phosphate groups on the enzyme substrate should optimally be done at a pH less than 7.

As used herein, the terms "redox-inactive reductive species," "redox-inactive reductive precursor," or "phosphorylated reducing agent" are all intended to mean the precursor to the reductive species/reducing agent, which under the proper conditions (i.e., the addition of the label enzyme) will reduce soluble metal ions such as silver (+1) or gold (+3) to a silver or gold atom such that it becomes visible to the eye as a specific dot under a brightfield light microscope. A particularly preferred redox-inactive reductive species of the present invention is ascorbate phosphate, which is alternatively recited herein as "ascorbic acid-2-phosphate" or "ascorbic acid phosphate." Ascorbate diphosphate can also be used. Another preferred redox-inactive reductive species is hydroquinone diphosphate. Other novel redox-inactive reductive species are taught herein.

As used herein, the term "reducing agent" means a chemical substance that can reduce soluble metal ions such as silver (+1) or gold (+3) to a silver or gold atom (metallic oxidation state 0) such that it becomes visible to the eye as a specific dot under a brightfield light microscope. Exemplary reducing agents that can be used in the methods and kits of the invention are hydroquinone, (a.k.a. hydroquinone dianion), ascorbic acid (a.k.a ascorbate), 2-aminophenol and 4-aminophenol. Other reducing agents are well-known to those of ordinary skill in the art, and can be substituted for those taught herein.

As used herein, the term "metal ion" is intended to include silver ion or gold ion. A particularly preferred metal ion is silver ion. When silver ion is used in the methods and kits of the invention, an optional gold ion pretreatment step may also be applied to enhance the silver deposition.

As used herein, the term "enzyme immunoassay (EIA)" is intended to include any assay used to immunologically detect and quantify the presence of antigens or antibodies of interest in a wide variety of biological samples. The term "ELISA-based assay" is a preferred type of EIA, and is intended to include all known variations of ELISA assays, including sandwich assays, antigen capture, antibody capture, competitive or blocking ELISAs, which are well-known to those skilled in the art.

As used herein, the term "nucleic acid array" or "nucleic acid microarray" refers to a solid support with at least one surface having a plurality of different nucleic acid sequences attached to the surface. DNA array technology is described in U.S. Pat. Nos. 6,600,031, 6,576,424, 6,203,989, 6,180,351, 6,156,501, 6,083,726, 5,981,185, 5,744,101, 5,677,195, 5,624,711, 5,599,695, 5,510,270, 5,445,934, 5,384,261, 5,571,639, 5,451,683, 5,424,186, 5,412,087, 5,384,261, 5,252,743 and 5,143,854; PCT WO 92/10092; PCT WO 93/09668; and PCT WO 97/10365, which are incorporated by reference in their entireties.

The development of the metal precipitate in the methods of the invention should be conducted at a pH of 2-10, preferably 3-9, and most preferably 3.8-7 in buffer such as, e.g., citrate buffer and in the presence of additional aliquots of silver ions. Alternatively, and preferably, the deposited metal precipitate can be developed or enhanced by using Sigma's Silver Enhancer Kit (Sigma Chemical Company, Product No. SE-100, ST. Louis, Mo.), or a similar commercially available product well-known to those skilled in the art. Several development procedures aimed at augmenting the size of the metal particles can also be found in "Gold and Silver Staining: Techniques in Molecular Morphology", edited by Gerhard W. Hacker and Jiang Gu, CRC Press, Boca Raton, Fla. (2002), at page 56. The incubation steps are conducted for a strictly controlled period of time after which the development may be quenched by the addition of thiosulfate or other sulfur-containing compounds well-known to those skilled in the art.

A gold pretreatment step may optionally be utilized in the methods of the invention to "seed" the area immediately adjacent to the immobilized alkaline phosphatase (or other label enzyme being used), thereby taking advantage of the well-known propensity for silver metal to deposit on a nucleation site such as gold particles ("metallography"). As demonstrated in Examples 3 and 4, below, once the SA-AP conjugate was bound to the biotinylated conjugate molecule, gold ion in the form of $AuCl_3$ together with ascorbate phosphate was co-deposited. AP dephosphorylated the ascorbate phosphate resulting in production of the reducing agent ascorbate, which then reduced gold ions to metallic gold. Metallic gold then served as the nucleation site for further amplification of the signal by silver ion reduction to silver metal.

The detection of the metallic silver precipitate can be accomplished by any of the multiple means available to those skilled in the art based on the type of assay employed: brightfield light microscopy (in the case of in situ histochemical detection), transmittance of the laser light from underneath the surface of the microplate (or other solid support), reflectance of the light directed from above the surface of the microplate (or other solid support), through the use of surface plasmon resonance technique, light scattering or surface enhanced fluorescence, or scanning densitometry.

Quantification of ELISA results is routinely accomplished by those skilled in the art, and generally relies on standard concentrations of the antigen or hapten one needs to quantify. By incubating the known concentrations of these standards with the capture antibody, washing, and secondary incubation with the conjugate antibody, one is able to construct a standard curve correlating the known concentration of the substance to be quantified with the elicited signal. The signal elicited from the unknown concentration of the sample is then interpolated on the standard curve allowing the reading of the concentration on the abscissa of the plot.

The present invention is also directed to novel compounds that have been specifically synthesized for use in the above methods as redox-inactive reductive species. Most preferred is ascorbic acid phosphate (see, general formula I wherein Z is $PO_3^{-2}$ substrate, which when dephosphorylated by its enzyme alkaline phosphatase, results in ascorbate ion, a good reducer of silver and gold cations. Generally, compounds having the formulas (I)-(VII) shown below are excellent substrates.

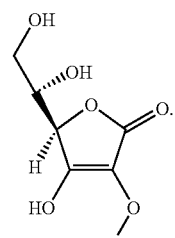

I

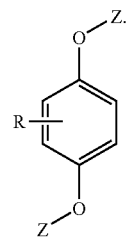

II

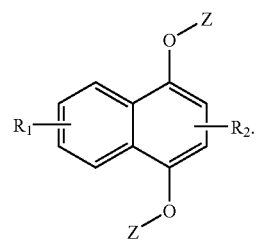

III

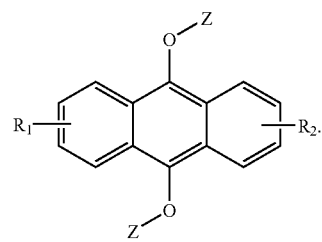

IV

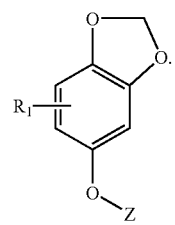

V

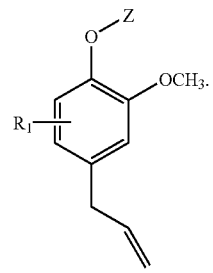

VI

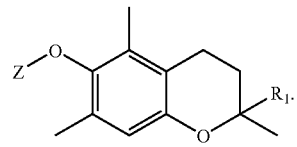

VII

For general structures II-VII, Z may be $PO_2^{2-}$, galactosyl, glucosyl, ester or beta-lactam. For general structures II-IV, one of the two Zs may also be H.

For general structures II-IV, at least one Z must be $PO_3^{2-}$, galactosyl, glucosyl, ester or beta-lactam.

For general structure II, R may be H, alkyl, aryl, carboxyl, carboxyalkyl, $NH_2$, $(CH_2)_n$—COOH—, nitro, ether, thioether or sulphonate.

For general structures III-VII, $R_1$ may be H, alkyl, aryl, carboxyl, carboxyalkyl, $NH_2$, $(CH_2)_n$—COOH—, nitro, ether, thioether or sulphonate.

For general structures III-IV, $R_2$ may be H, alkyl, aryl, carboxyl, carboxyalkyl, $NH_2$, $(CH_2)_n$—COOH—, nitro, ether, thioether or sulphonate.

Thus, the invention disclosed herein utilizes a novel series of phosphates, diphosphates and related derivatives which, although completely inactive as reducing agents, become reactive and capable of reducing metal ions to metallic oxidation state (0) after the alkaline phosphatase-catalyzed hydrolysis of the phosphate groups. The redox-inactive reductive species shown in the structures below is ascorbic acid phosphate (a.k.a. "ascorbate phosphate"), a particularly preferred embodiment. In the presence of alkaline phosphatase, ascorbic acid phosphate is hydrolyzed to the active reducing agent ascorbic acid, which is capable of reducing gold, silver and other metal cations to metal (0):

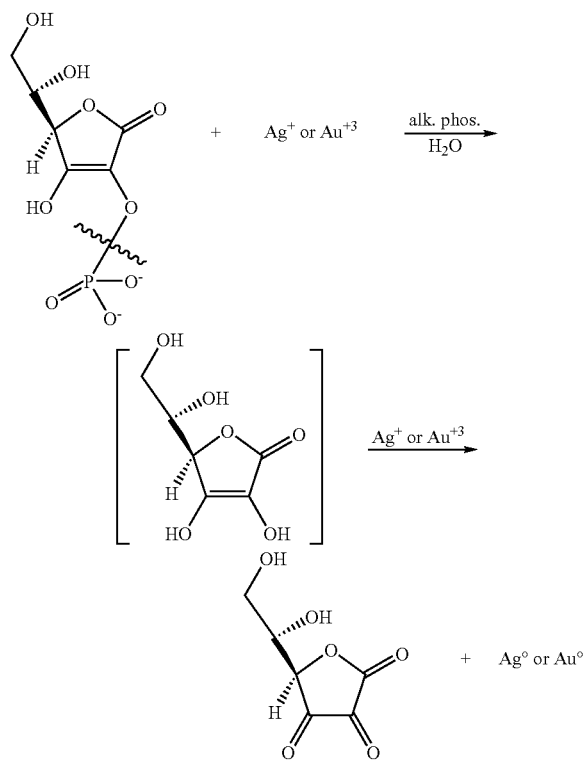

Still other novel organic reducing agent precursors include α-tocopherol phosphate, sesamol phosphate and eugenol phosphate, shown in the general structures V-VII, wherein $Z=PO_3^{-2}$; and R may be H, alkyl, aryl, carboxyl, carboxyalkyl, $NH_2$, $(CH_2)_n$—COOH—, nitro, ether, thioether or sulphonate.

In a particularly preferred embodiment of the invention, the enzyme label is alkaline phosphatase and the redox-inactive reducing species is ascorbate phosphate. In this combination, ascorbate phosphatase is the "substrate" for alkaline phosphatase. There are several advantages of using alkaline phosphatase as a label and ascorbate phosphate as the substrate in the present invention:

(1) alkaline phosphatase is one of the perfectly evolved enzymes with a Kcat/Km approximating the diffusion-controlled limit of $1 \times 10^9$ liter/mole-sec;

(2) alkaline phosphatase's optimal pH is 9-10, coinciding with the fastest reduction potentials of the hydroquinones liberated by the dephosphorylation of the substrates;

(3) aryl and alkyl phosphates and diphosphates can be synthesized reasonably inexpensively;

(4) aryl and alkyl phosphates and diphosphates are excellent substrates of alkaline phosphatase;

(5) aryl and alkyl phosphates and diphosphates are generally reasonably stable and can be formulated to resist decomposition over extended periods;

(6) alkaline phosphatases are very stable enzymes resisting thermal and chemical degradation better than most enzymes;

(7) alkaline phosphatases are reasonably small and methods of conjugation to other biological molecules have been developed; and (8) ascorbic acid phosphate is an excellent substrate of AP and ascorbate has a very high reduction potential, i.e., it reduces $Ag^+$ and $Au^{+3}$ quantitatively and rapidly, with dehydroascorbate as the only by-product.

Another excellent reducing agent is hydroquinone dianion. The structures below show the hydroquinone-benzoquinone equilibrium structures, at a pH of from 9-10, in the presence of an electron acceptor like silver cation. Hydroquinone dianion is the actual species responsible for reducing silver cations to insoluble metal. The formation of benzoquinone is favored at high pH:

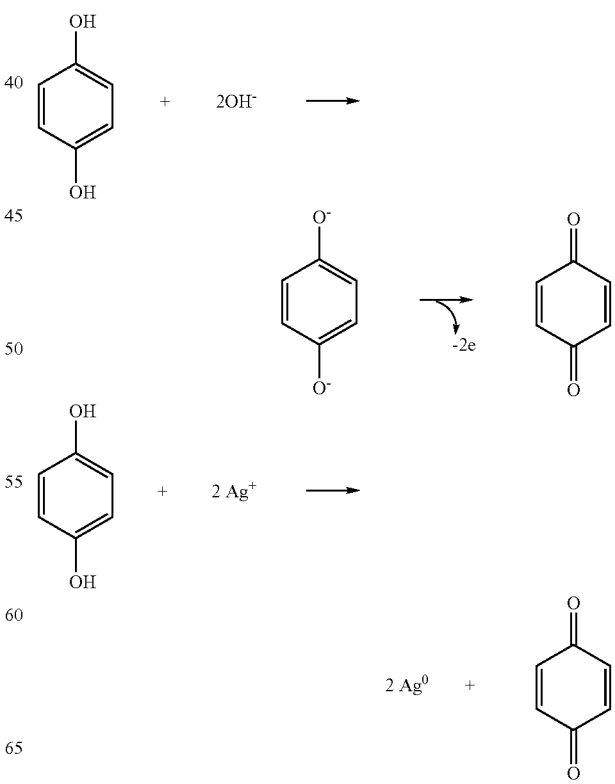

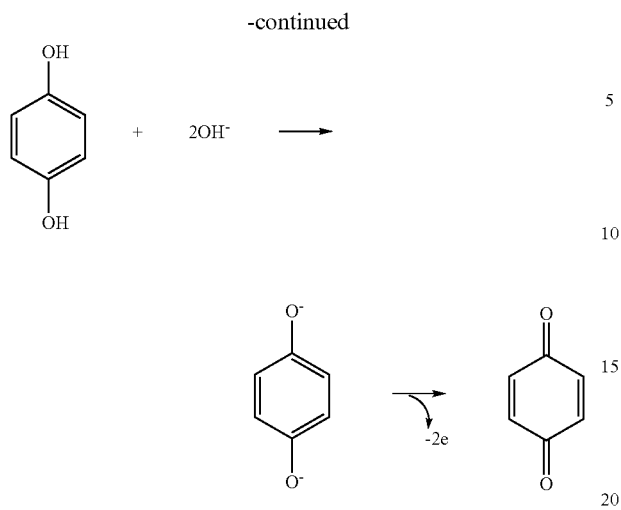

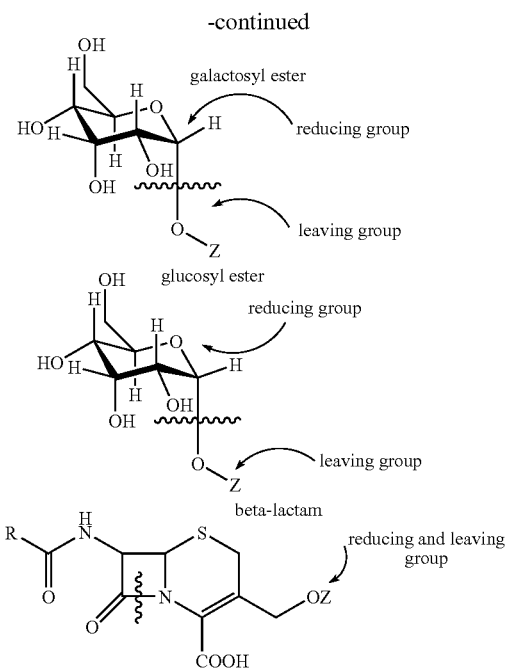

General structures II-IV, above, are some hydroquinone derivatives that are also the subject of this invention. Hydroquinone diphosphate (general structure II with both Zs=phosphate) is a preferred substrate for dephosphorylation by the enzyme alkaline phosphatase, which at pH 7-11 is dephosphorylated to hydroquinone dianion, a preferred reducing agent for silver cation. Other hydroquinone-like derivatives are depicted in general structures III-IV, and are naphthohydroquinone (III), and anthrahydroquinone (IV). They can be substituted as shown within the aryl rings at any position with $R_1$ and $R_2$, and at the oxygens with Z. Substituents $R_1$ and $R_2$ can be just about any moiety that can be reacted at these sites, yet still retain the ability to generate a dianion at the desired pH. An exhaustive list of organic substituents is not included herein, but some likely substituents include the following: H, alkyl, aryl, carboxyl, carboxyalkyl, $NH_2$, $(CH_2)_n$—COOH—, nitro, ether, thioether and sulphonate.

Besides alkaline phosphatase and its substrate phosphates of various reducing agents, other enzyme labels may also be used in the present invention, depending upon the label-substrate. For example, esterases may be used in conjunction with mono and diesters of carboxylic acids. Galactosidases and glucosidases may also be employed for deprotection of the substrates mono- and di-galactosides and mono- and di-glucosides. The "Z" groups, which are shown below together with the linking oxygen bridging atom, may form a reducing substance or a leaving group.

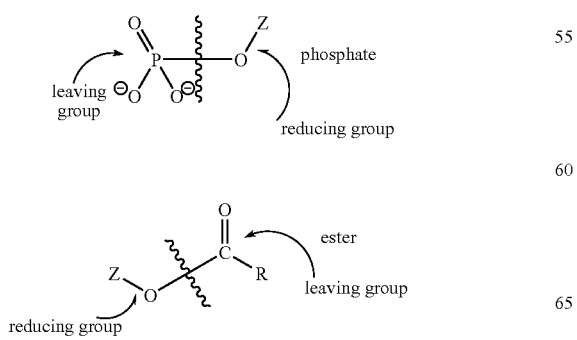

The last structure, a C3' beta-lactam (i.e., cephalosporin, a preferred beta-lactam), may also be used in conjunction with beta-lactamases as enzyme labels. The R group of the beta-lactams may be an alkyl aryl, i.e., thiophene, methyl or benzyl.

Of particular value and interest are the galactosyl, glucosyl and other saccharide hydroquinone and ascorbate derivatives in that the enzyme turnover of the inactive substrate yields TWO reducing agents, namely hydroquinone or ascorbate and the carbohydrate with its reducing end also capable of reducing the silver ion to metallic silver:

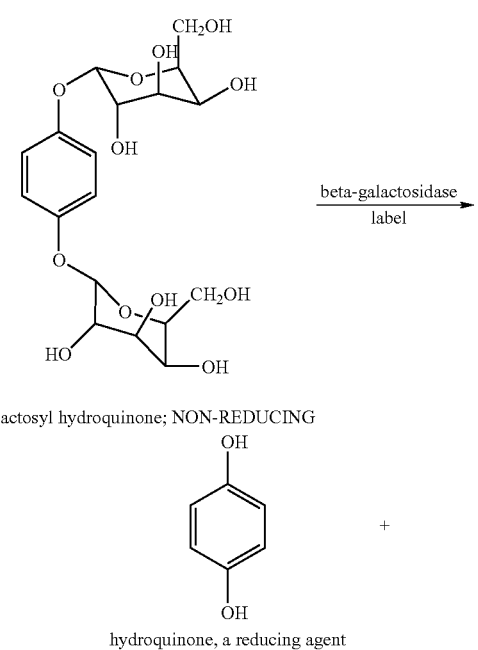

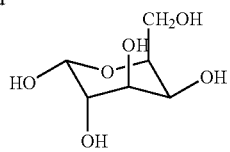

beta-galactose, a reducing sugar

In embodiments of the invention relating to a method for the enhanced detection of analytes using an ELISA-based assay in a microtiter plate or other suitable solid phase, there are many proteins and other biological molecules whose detection and quantification is crucially important in diagnostic medicine. The sample tested in the present invention is generally a biological sample, such as whole blood, serum, plasma, urine, saliva, spinal fluid, fecal matter, or puncture fluid. The object of measurement contained in the sample is generally an antigen or antibody, for example, plasma protein such as albumin, immunoglobulin or complement; a tumor-related antigen such as alpha-fetoprotein (AFP), CA19-9, carcinoembryonic antigen (CEA), prostatic acid phosphatase (PAP), prostate specific antigen (PSA), beta-human chorionic gonadotropin (hCG); infectious disease-related antigen/antibody such as hepatitis B, hepatitis C, syphilis, HIV or CRP; blood coagulation fibrinolysis-related substance such as fibrin/fibrinogen degradation product, D dimer or antithrombin III; myocardial infarction-related protein such as myoglobin or CK-MB; hormones such as thyroid stimulating hormone (TSH), follicle stimulating hormone (FSH), thyroxine (T4), insulin or human chorionic gonadotropin (HCG); or prescription drugs, such as digoxin or theophylline, or illegal drugs, such as cocaine. Similarly, detection of specific epitopes on the surface of the cells is of great importance. Ultrasensitive quantification is important in assessing these analytes in biological samples.

Figure 14:
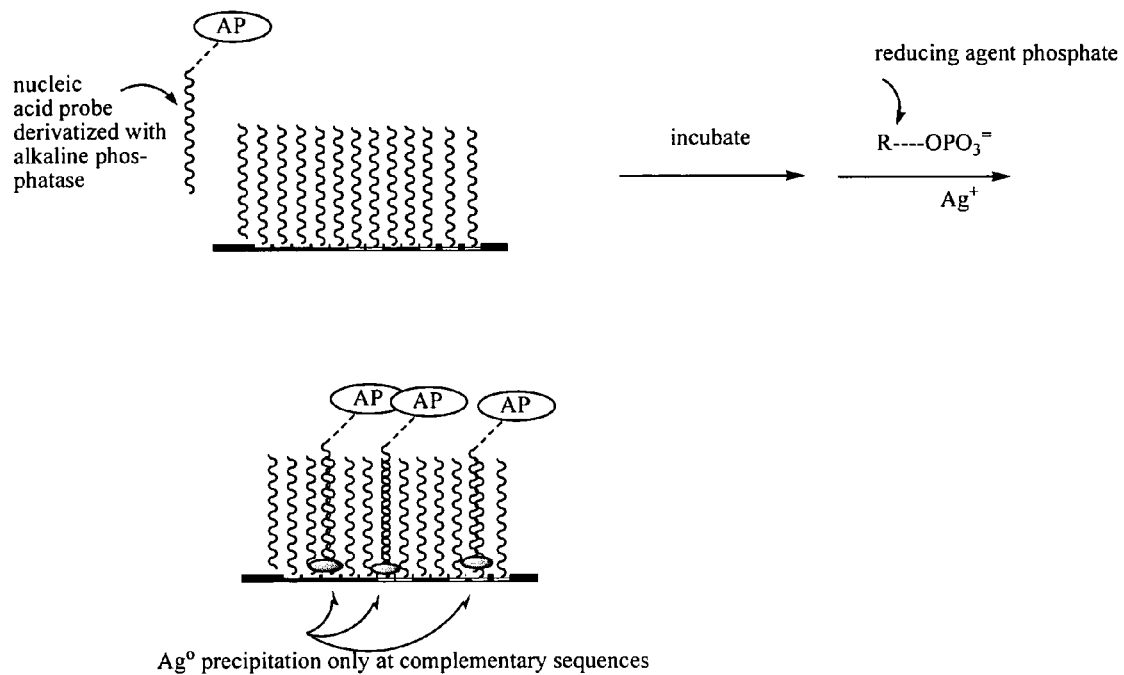
FIG. 14 is a schematic representation of an embodiment of the invention, whereby enzyme-catalyzed metal deposition is used for the enhanced detection of nucleic acids arrayed on a slide. A nucleic acid probe would be labeled with alkaline phosphatase and the DNA arrayed on a slide would be hybridized with the nucleic acid probe. After washings and upon addition of silver ions and phosphorylated reducing agent, the sites displaying deposited silver would specifically and clearly indicate complementary strands.

Furthermore, enzyme metallographic silver deposition taught by the present invention can be employed in high throughput detection of agonists and antagonists binding to the cognate receptors, which is very important in the practice of modern medicinal chemistry, high throughput screening of pharmaceuticals, receptor-ligand interactions, and hybridization assays involving nucleic acid array technology (see, FIG. 14 which illustrates schematically the principle applied to the detection of complementary nucleic acids).

The following examples are included for purposes of illustrating certain aspects of the invention and should not be construed as limiting.

EXAMPLE 1

Phosphates for Alkaline-Phosphatase Mediated Reduction of Silver (I)

Figure 1:
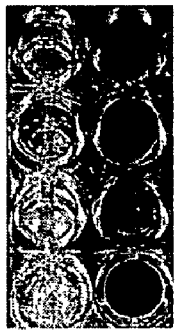
FIG. 1 is a photograph of eight microtiter wells arranged in two columns of four. Column A is the control column containing 100 µL of 50 mM silver nitrate and 100 µL of 50 mM phosphate substrate in 100 mM tris, pH 9.0. Column B contains the same components with the addition of 5 µL of 0.2 mg/mL calf-intestinal alkaline phosphatase (Pierce) in 100 mM Tris, pH 7.0. Column B demonstrates the action of alkaline phosphatase-mediated release of the reducing substrate (i.e., ascorbic acid-2-phosphate to ascorbic acid) and the concomitant reduction of silver nitrate to silver metal particles by the released reducing substrate.

Silver nitrate (100 μL of 50 mM AgNO$_3$) was aliquoted into the wells of a microtiter plate (see FIG. 1). Addition of 100 μL of a 50 mM solution of either ascorbic acid-2-phosphate (wells A1, B1), sesamol phosphate (wells A2, B2), hydroquinone-1,4-diphosphate (wells A3, B3), or 2,2,5,7,8-pentamethyl-6-chromanol phosphate (wells A4, B4) to the silver solution did not elicit any reaction. If calf-intestinal alkaline phosphatase (5 μL of 0.2 mg/mL) was added to the Column B wells, each solution formed metallic silver (0) as either a fine, black precipitate or silvering of the container walls.

Column A: 100 μL of 50 mM AgNO$_3$ and 100 μL of 50 mM substrate phosphate.

Column B: 100 μL of 50 mM AgNO$_3$, 100 μL of 50 mM substrate phosphate, and 5 μL of 0.2 mg/mL calf-intestinal alkaline phosphatase (Pierce Chemical, Rockford, Ill.) in 100 mM Tris, pH 7.0.

EXAMPLE 2

Figure 2:
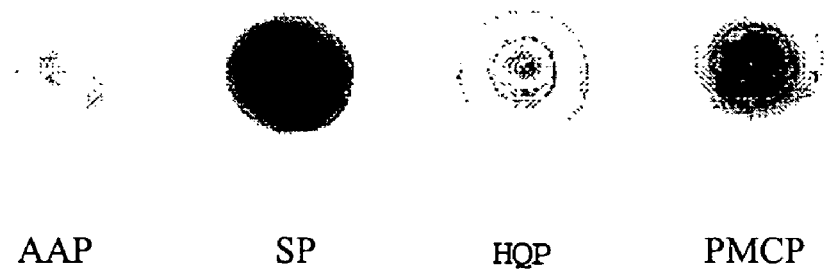
FIG. 2 is a photograph of four spots on nitrocellulose paper that were treated with 5 µL of 0.2 mg/mL calf-intestinal alkaline phosphatase (Pierce) in 100 mM Tris, pH 7.0, 5 µL of a 50 mM solution of the phosphates from Example 1 in 100 mM Tris, pH 9.0, and 5 µL of 50 mM silver nitrate. The following abbreviations are used: Ascorbic acid-2-phosphate (AAP), Sesamol phosphate (SP), Hydroquinone-1,4-diphosphate (HQP), 2,2,5,7,8-Pentamethyl-6-chromanol phosphate (PMCP).

Alkaline Phosphatase, Silver Nitrate, and Substrate Phosphates on Nitrocellulose Alkaline phosphatase (5 μL of 0.2 mg/mL) was added to nitrocellulose paper and dried (see FIG. 2). Each of the phosphates were spotted on the nitrocellulose as 5 μL of 0.05M solution in 0.1M Tris, pH 9. When 5 μL of 0.05M AgNO$_3$ was added to each dried spot, a black precipitate was observed only at the spot where alkaline phosphatase was applied.

EXAMPLE 3

Offline Development of Ag Nanoparticles on Tonsil Using the AP-SA Conjugate at High pH The preparation of the slides for analysis was done on a Ventana Benchmark® automated staining instrument (Ventana Medical Systems, Inc., Tucson, Ariz.). The slides were removed for manual development of signal. The use of the term "buffer" within this Example refers to a 0.1 M Tris buffer (Trizma base (Sigma-Aldrich) in dI H$_2$O pH to 9 using glacial acetic acid (Sigma-Aldrich). The following is the adapted procedure from the instrument: the paraffin-coated tissue on the slide was heated to 75° C. for 4 minutes and treated twice with EZPrep™ (Ventana, Tucson, Ariz.) volume adjusted at 75° C. before application of the liquid cover slip with EZPrep volume adjust. After 4 minutes at 75° C., the slide was rinsed and automated deparaffinization volume adjust was added along with liquid cover slip to deparaffinize the tissue at 76° C. for 4 minutes. The slide was cooled to 40° C. and rinsed three times before the addition of ANTI-CD20 antibody (clone L26, Ventana, Tucson, Ariz.) followed by liquid cover slip and incubation at 40° C. for 16 minutes. After rinsing the slide, the tissue was treated with biotinylated Universal Secondary Antibody (Ventana Medical Systems, part #760-4205) to co-locate biotin with the Anti-CD20 antibody, followed by liquid cover slip and incubation at 40° C. for 8 minutes. The slide was rinsed twice and removed from the instrument and stored in 1× Reaction Buffer (Ventana, Tucson, Ariz.) until they were ready to be developed.

The slide was removed from 1× Reaction Buffer and rinsed 10 times with buffer followed by the addition of 300 μL of buffer to the slide as well as 100 μL of AP-SA conjugate (0.14 mg/mL in buffer, Sigma-Aldrich). The slide was incubated at 37° C. for 15 minutes followed by rinsing ten times with buffer. The slide was treated with 300 μL of the buffer followed by 50 μL of AuCl$_3$ (Sigma-Aldrich) (2.5 μg/mL in buffer) and 50 μL of ascorbic acid phosphate (Sigma-Aldrich) (0.1 M in buffer). The slide was incubated at 37° C. for 20 minutes and followed by rinsing 10 times with buffer. The slide was treated with 300 μL of buffer followed by 50 μL of silver acetate (Sigma-Aldrich) (0.1 M in buffer) and 50 μL of the ascorbic acid phosphate solution and incubated at 37° C. for 20 minutes. The slide was again rinsed 10 times with buffer followed by the application of ISH Red Counterstain (Ventana, Tucson, Ariz.) as a counter-stain. The slide was incubated with the counter-stain for 3 minutes and rinsed with buffer. Dehydration of the slide with ethanol and xylene preceded the application of the coverslip, after which the slides were viewed under the microscope.

Figure 3:
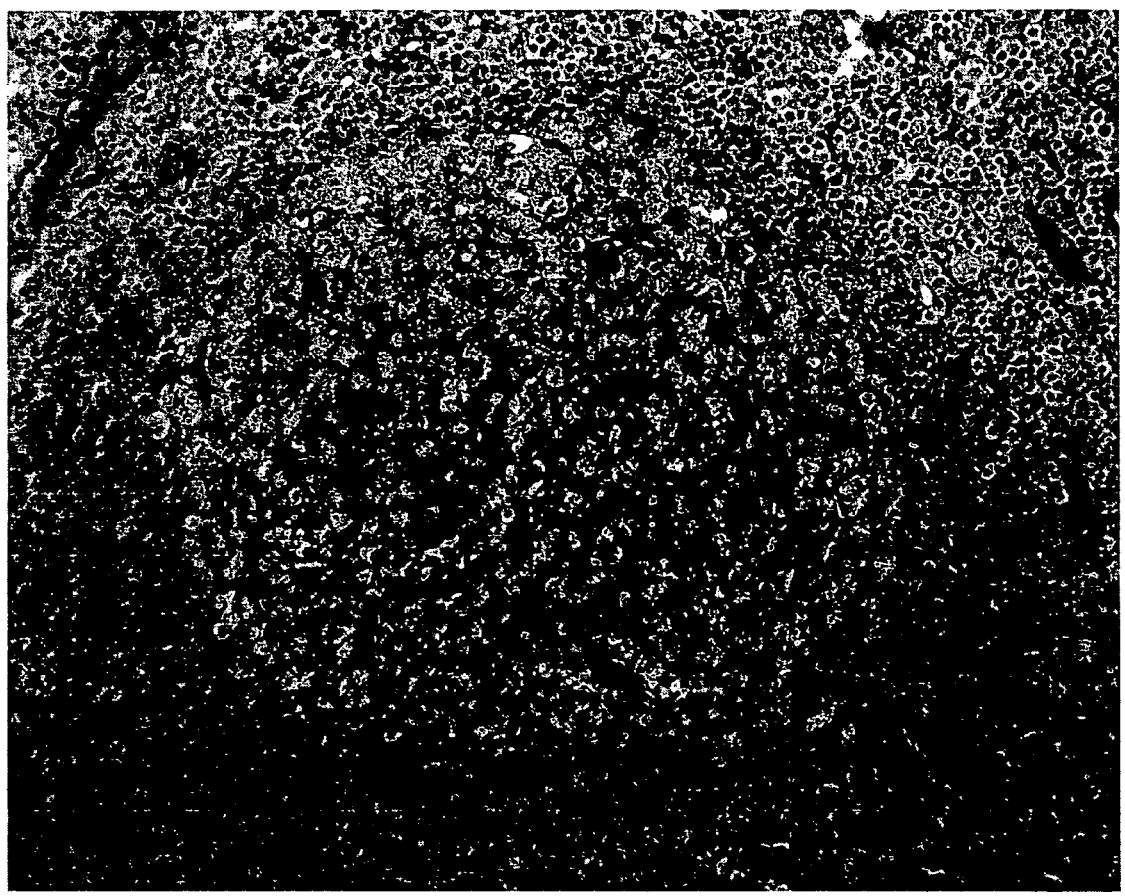
FIG. 3 is a gray-scale photomicrograph of normal tonsil tissue stained using AP-SA conjugate, gold pre-treatment, and silver reduction using ascorbic acid-2-phosphate (AAP).
Figure 5:
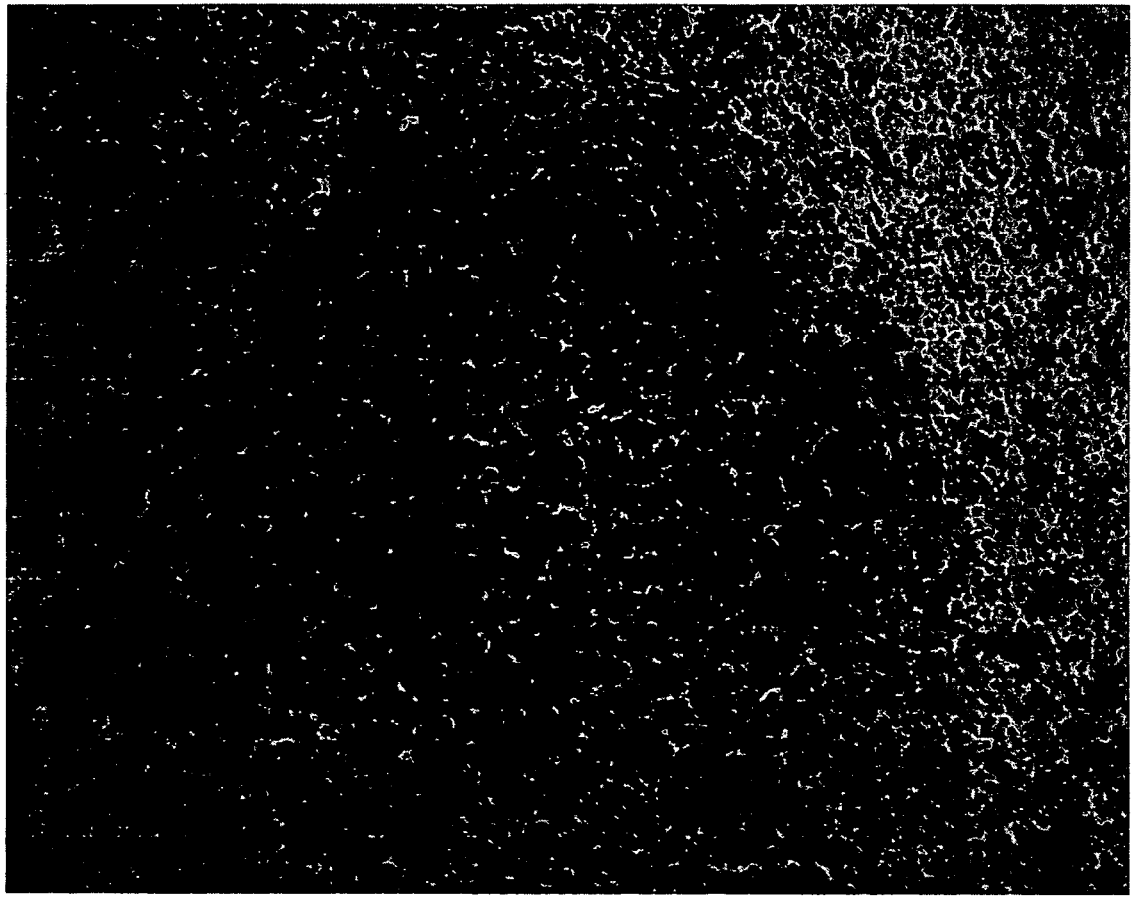
FIG. 5 is a gray-scale photomicrograph of the positive control for FIGS. 3-4.

As shown by the gray-scale photographs in FIG. 3, staining is present in the plasma membrane and cytoplasmic regions of normal B cells in normal tonsil. Staining intensity is comparable to positive control (FIG. 5) detected with Enhanced V-Red Detection kit (Ventana, Tucson, Ariz.).

EXAMPLE 4

Online Development of Ag Nanoparticles on Tonsil Using the AP-SA Conjugate at High pH The main difference between this example and Example 3 is that this example shows full automation of the staining steps, while in Example 3 the slide was removed from the instrument prior to development with AP-SA. The preparation of the slides for analysis was done on a Ventana Benchmark Instrument. The use of the term "buffer" within this Example refers to a 0.1 M Tris buffer (Trizma base-Sigma-Aldrich) in deionized $H_2O$, pH to 9 using glacial acetic acid (Sigma-Aldrich). The following is the adapted procedure from the instrument: the paraffin-coated tissue on the slide was heated to 75° C. for 4 minutes and treated twice with EZPrep volume adjust at 75° C. before application of the liquid cover slip with EZPrep volume adjust. After 4 minutes at 75° C., the slide was rinsed and automated deparaffinization volume adjust was added along with liquid cover slip to deparaffin the tissue at 76° C. for 4 minutes. The slide was cooled to 40° C. and rinsed three times before the addition of ANTI-CD20 antibody (clone L26, Ventana, Tucson, Ariz.) followed by liquid cover slip and incubation at 40° C. for 16 minutes. After rinsing the slide, the tissue was treated with biotinylated Universal Secondary Antibody (Ventana Medical Systems, part #760-4205) to co-locate biotin with the Anti-CD20 antibody, followed by liquid cover slip and incubation at 40° C. for 8 minutes. The slide was rinsed twice with buffer followed by the application of liquid cover slip and the addition of AP-SA conjugate (Sigma-Aldrich, 100 µL, 0.14 mg/mL in buffer) and incubation at 37° C. for 16 minutes. The slide was rinsed with buffer, liquid cover slip was applied and this was followed by the addition of 100 µL of a 1:1 solution of $AuCl_3$ (Sigma-Aldrich) (1.25 µg/mL) and ascorbic acid phosphate (Sigma-Aldrich) (0.05 M) in buffer. The slide was incubated at 37° C. for 20 minutes, rinsed with buffer and coated with liquid cover slip. A total of 100 µL of a 1:1 solution of silver acetate (Sigma-Aldrich) (0.05 M) and ascorbic acid phosphate (0.05 M) was added to the slide, and the slide was incubated for 20 minutes at 37° C. The slide was rinsed three times with buffer and treated to a detergent wash before dehydration with ethanol and xylene and subsequent application of a cover slip to the slide, after which the slide was viewed through a microscope.

Figure 4:
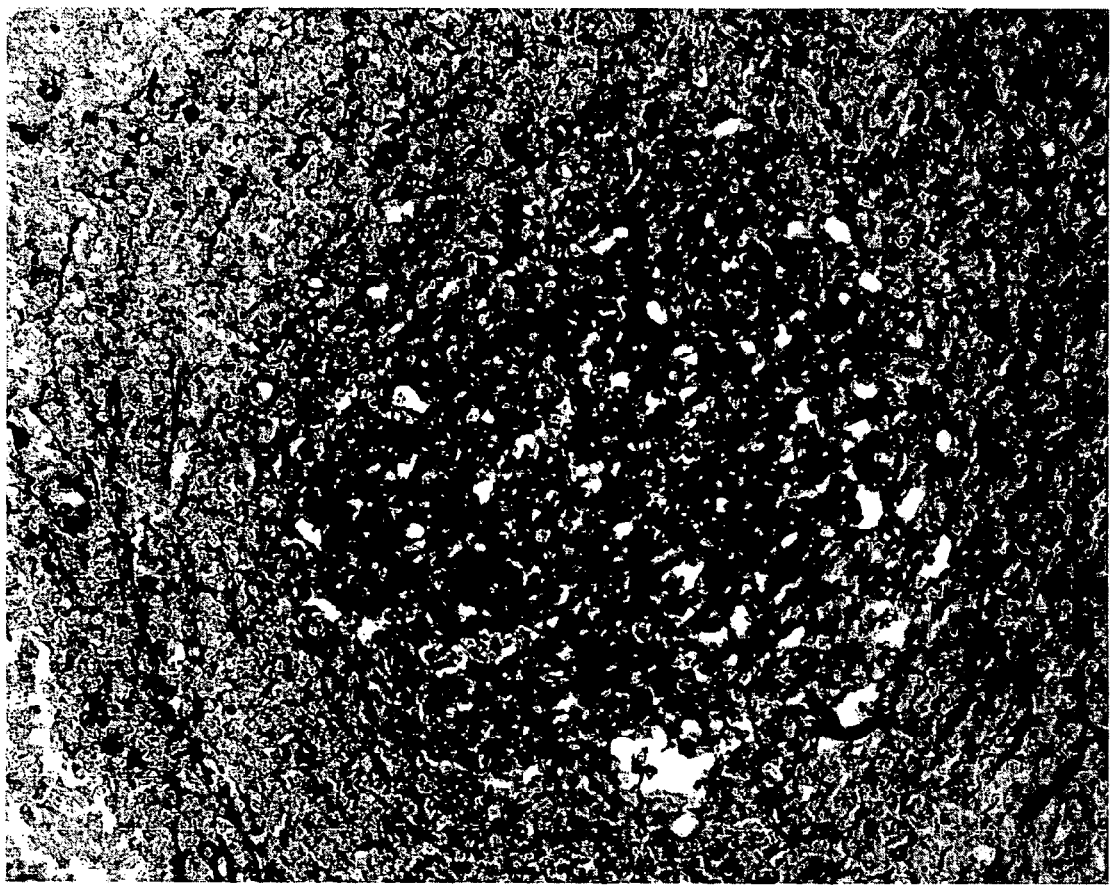
FIG. 4 is a gray-scale photomicrograph of normal tonsil tissue stained using AP-SA conjugate, gold pre-treatment, and silver reduction using AAP, the only difference from FIG. 3 being full online development of the silver signal.

As shown by the gray-scale photographs in FIG. 4, staining is present in the plasma membrane and cytoplasmic regions of normal B cells in normal tonsil. Staining intensity is comparable to positive control (FIG. 5) detected with Enhanced V-Red Detection kit (Ventana, Tucson, Ariz.).

EXAMPLE 5

Anti-Desmin on Skeletal Muscle

Figure 6:
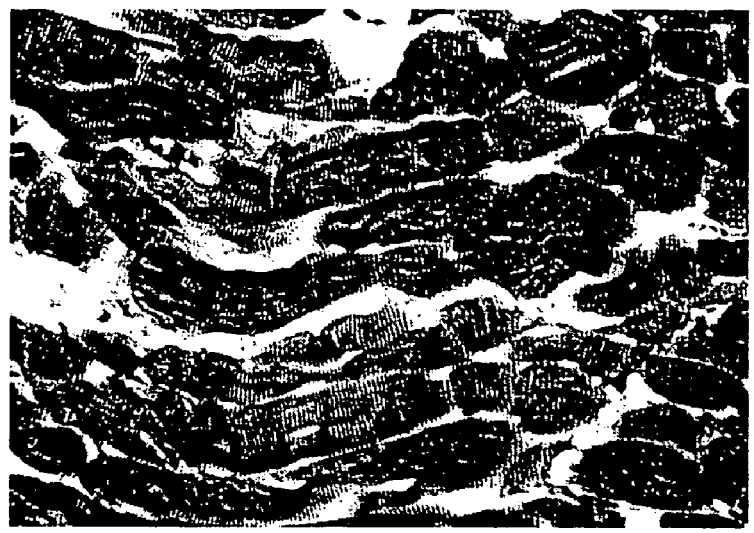
FIG. 6 is a photomicrograph of anti-Desmin antibody on skeletal muscle detected with gold pre-treatment, AAP and AgNO$_3$, 20 minutes incubation.

Formalin-fixed, paraffin-embedded skeletal muscle was sectioned and placed on glass slides for light microscopy. Sections were deparaffinized on a Ventana Medical Systems' BenchMark slide stainer. Remaining on the BenchMark, the section was treated with Protease 1 (Ventana) for 4 minutes. Sections were then incubated with Anti-Desmin (Ventana, cat#760-2513) monoclonal antibody for 16 minutes at 37° C. After washing with Reaction Buffer on the instrument, a rabbit anti-mouse antibody was incubated for 8 minutes at 37° C. Sections were then rinsed with Reaction Buffer and incubated with a mouse anti-rabbit antibody for 8 minutes at 37° C. (Amplification Kit, Ventana cat. no. 760-080). Next the sections were rinsed with Reaction Buffer and incubated with a cocktail of biotinylated secondary antibodies biotinylated Universal Secondary Antibody (Ventana Medical Systems, part #760-4205) for 8 minutes at 37° C. The sections were rinsed and a solution of streptavidin-alkaline phosphatase (Enhanced SA-/Alk Phos/VRed Ventana, cat. no. 253-2181) was incubated for 16 minutes at 37° C. The sections were then removed from the BenchMark slide stainer. The slides were then washed with dI $H_2O$ and incubated with 500 µl of 2.5 µg/ml hydrogen tetrabromoaurate (III) hydrate (Aldrich cat. no. 44,212) for 4 minutes at 37° C. The solution was rinsed with $dIH_2O$ and 250 µl of 50 mM $AgNO_3$ (Sigma #S-0139) in 0.5 M Tris Buffer at pH 9.0 and 250 µl of 100 mM ascorbic acid phosphate (Sigma A-8960) in a 0.5M DEA Buffer at pH 10.0 with 5% PVA (av. mol wt 70,000 to 100,000 Sigma #P-1763) was applied to each section. The slides were allowed to incubate for 20 minutes at 37° C. The slides were rinsed with dl $H_2O$ and coverslipped without counterstain. Results are shown in FIG. 6.

EXAMPLE 6

Anti-S 100 on Brain

Figure 7:
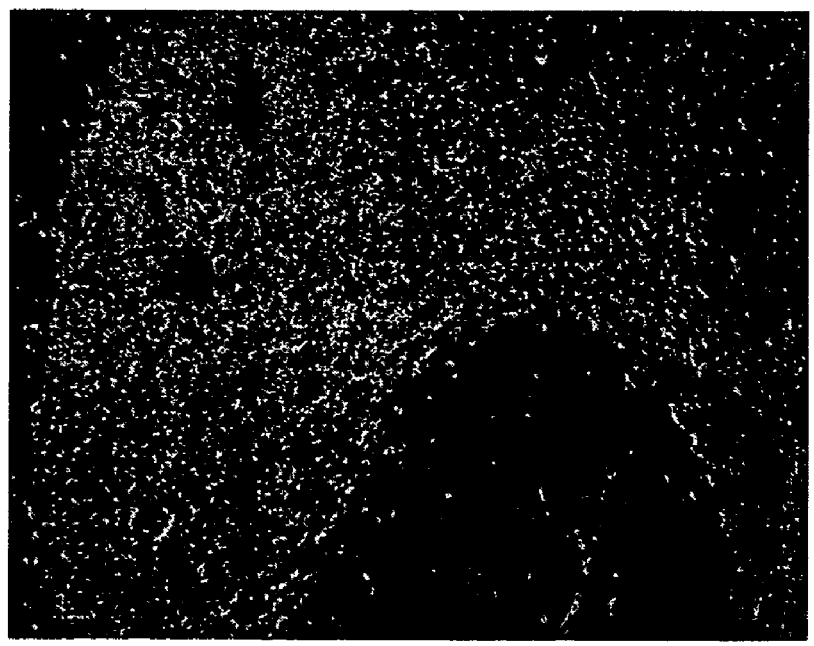
FIG. 7 is a photomicrograph of anti-S100 on brain, detected with gold pre-treatment, AAP and AgNO$_3$, 20 minutes incubation.

Formalin-fixed paraffin-embedded brain tissue was sectioned and placed on glass slides for light microscopy. Sections were deparaffinized on a Ventana BenchMark slide stainer. Sections were then incubated with Anti-S100 polyclonal antibody (Ventana cat. no. 760-2523) for 16 minutes at 37° C. Next the sections were rinsed with Reaction Buffer and incubated with a cocktail of biotinylated secondary antibodies biotinylated Universal Secondary Antibody (Ventana Medical Systems, part #760-4205) for 8 minutes at 37° C. The sections were rinsed and a solution of streptavidin-alkaline phosphatase (Enhanced SA-/Alk Phos/VRed Ventana, cat. no. 253-2181) was incubated for 16 minutes at 37° C. The sections were then removed from the BenchMark slide stainer. The slides were then washed with dI $H_2O$ and incubated with 500 µl of 2.5 µg/ml hydrogen tetrabromoaurate (E) hydrate (Aldrich #44,212) for 4 minutes at 37° C. The solution was rinsed with $dIH_2O$ and 250 µl of 50 mM $AgNO_3$ (Sigma #S-0139) in 0.5 M Tris Buffer at pH 9.0 and 250 µl of 100 mM ascorbic acid phosphate in a 0.5M (Sigma A-8960) DEA Buffer at pH 10.0 with 5% PVA (av. mol wt 70,000 to 100,000 Sigma #P-1763)) was applied to each section. The slides were allowed to incubate for 20 minutes at 37° C. The slides were counterstained with Nuclear Fast Red and coverslipped. Results are shown in FIG. 7.

EXAMPLE 7

Rabbit Negative Control on Brain

Formalin-fixed paraffin-embedded skeletal muscle was sectioned and placed on glass slides for light microscopy. Sections were deparaffinized on a Ventana BenchMark slide stainer. Sections were then incubated with Rabbit Negative Control (Ventana, cat. no. 760-2023) for 16 minutes at 37° C. Next the sections were rinsed with Reaction Buffer and incubated with a cocktail of biotinylated secondary antibodies biotinylated Universal Secondary Antibody (Ventana Medical Systems, part #760-4205) for 8 minutes at 37° C. The sections were rinsed and a solution of streptavidin-alkaline phosphatase (Enhanced SA-/Alk Phos/VRed Ventana, cat. no. 253-2181) was incubated for 16 minutes at 37° C. The sections were then removed from the BenchMark slide stainer. The slides were then washed with dI $H_2O$ and incubated with 500 µl of 2.5 µg/ml hydrogen tetrabromoaurate (III) hydrate (Aldrich #44,212) for 4 minutes at 37° C. The solution was rinsed using di$H_2O$ and 250 µl of 50 mM $AgNO_3$ (Sigma #S-0139) in 0.5 M Tris Buffer at pH 9.0 and 250 µl of 100 mM ascorbic acid phosphate (Sigma A-8960) in a 0.5M DEA Buffer at pH 10.0 with 5% PVA (av. mol wt 70,000 to 100,000 Sigma #P-1763)) was applied to each section. The slides were allowed to incubate for 20 minutes at 37° C. The slides were counterstained with Nuclear Fast Red and coverslipped. Results are shown in FIG. 8.

Figure 8:
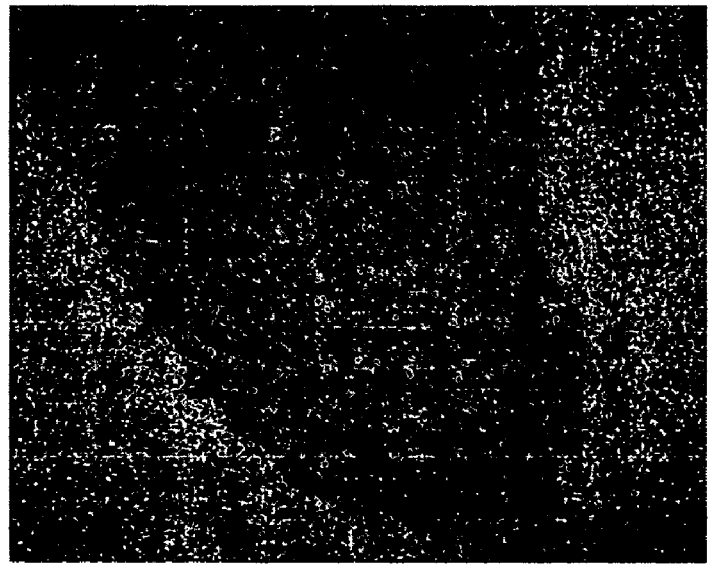
FIG. 8 is a photomicrograph of Rabbit Negative Control on brain detected with gold pre-treatment, AAP, and AgNO$_3$, 20 minutes incubation.
Figure 9:
FIG. 9 is a photomicrograph of anti-S100 antibody on brain tissue, using Ventana VRed detection.

The grey-black staining observed with FIG. 7 compared to the lack of grey-black staining observed with FIG. 8 demonstrates that the staining pattern in FIG. 7 is specific for the antigen since FIG. 8 was run with Negative Rabbit Control. FIG. 9 is the same case of brain tissue run with Anti-S100 but detected utilizing Ventana's Enhanced V-Red Detection Kit. Observe that the staining pattern is the same as that found in FIG. 7.

EXAMPLE 8

Anti-Desmin on Skeletal Muscle with Non-Enzymatic Amplification

Figure 10:
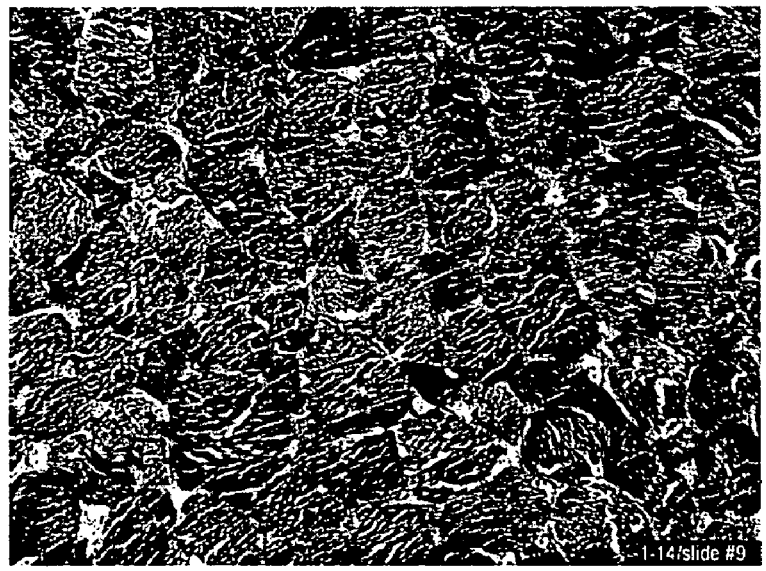
FIG. 10 is a photomicrograph of anti-Desmin antibody on skeletal muscle, gold pre-treatment, AAP, and AgNO$_3$, 10 minutes incubation, and 10 minutes of 4-methylaminophenol amplification.

This example shows that chemical amplification of the silver signal can be used to amplify the original silver deposited as a function of reduction by ascorbate. Formalin-fixed paraffin-embedded skeletal muscle was sectioned and placed on glass slides for light microscopy. Sections were deparaffinized on a Ventana BenchMark slide stainer. Remaining on the BenchMark, the section was treated with Protease 1 (Ventana) for 4 minutes. Sections were then incubated with Anti-Desmin (Ventana, cat. no. 760-2513) monoclonal antibody for 16 minutes at 37° C. After washing with Reaction Buffer on the instrument, a rabbit anti-mouse antibody was incubated for 8 minutes at 37° C. Sections were then rinsed with Reaction Buffer and incubated with a mouse anti-rabbit antibody for 8 minutes at 37° C. (Amplification Kit, Ventana cat. no. 760-080). Next the sections were rinsed with Reaction Buffer and incubated with a cocktail of biotinylated secondary antibodies biotinylated Universal Secondary Antibody (Ventana Medical Systems, part #760-4205) for 8 minutes at 37° C. The sections were rinsed and a solution of streptavidin-alkaline phosphatase (Enhanced SA-/Alk Phos/VRed, Ventana cat. no. 253-2181) was incubated for 16 minutes at 37° C. The sections were then removed from the BenchMark slide stainer. The slides were then washed with dI $H_2O$ and incubated with 500 µl of 2.5 µg/ml hydrogen tetrabromoaurate (III) hydrate (Aldrich #44,212) for 4 minutes at 37° C. The solution was rinsed with dI$H_2O$ and 250 µl of 50 mM $AgNO_3$ (Sigma #S-0139) in 0.5 M Tris Buffer at pH 9.0 and 250 µl of 100 mM ascorbic acid phosphate (Sigma A-8960) in a 0.5M DEA Buffer at pH 10.0 with 5% PVA (av. mol wt 70,000 to 100,000 Sigma #P-1763)) was applied to each section. The slides were allowed to incubate for 10 minutes at 37° C. The slides were rinsed with dI $H_2O$. The signal was then amplified by incubating for 10 minutes at 37° C. in a 25 mM 4-Methyl aminophenol (Aldrich #129720), 12 mM $AgNO_3$ solution in a 0.1 M Citrate Buffer at pH 3.8. FIG. 10 demonstrates the signal with the amplification when compared to Example 9 (FIG. 11) which is without any non-enzymatic amplification.

EXAMPLE 9

Anti-Desmin on Skeletal Muscle without Non-Enzymatic Amplification

Figure 11:
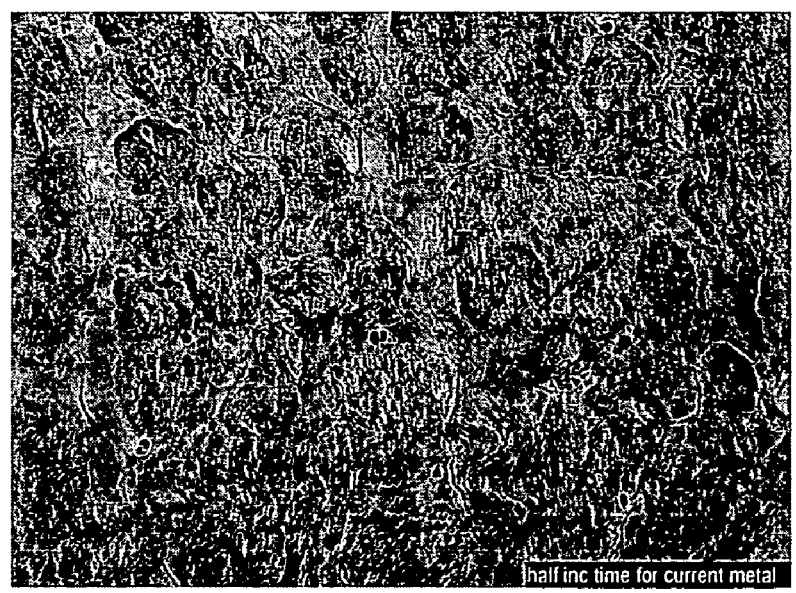
FIG. 11 is a photomicrograph of anti-Desmin antibody on skeletal muscle without any non-enzymatic amplification. The same conditions as in FIG. 10 were used, except no amplification step.

Formalin-fixed paraffin-embedded skeletal muscle was sectioned and placed on glass slides for light microscopy. Sections were deparaffinized on a Ventana Medical Systems' BenchMark slide stainer. Remaining on the BenchMark, the section was treated with Protease 1 for 4 minutes. Sections were then incubated with Anti-Desmin monoclonal antibody for 16 minutes at 37° C. After washing with Reaction Buffer, on the instrument, a rabbit anti-mouse antibody was incubated for 8 minutes at 37° C. Sections were then rinsed with Reaction Buffer and incubated with a mouse anti-rabbit antibody for 8 minutes at 37° C. Next the sections were rinsed with Reaction Buffer and incubated with a cocktail of biotinylated secondary antibodies. The sections were rinsed and a solution of Strept-Avidin Alkaline Phosphatase was incubated for 16 minutes. The sections were then removed from the BenchMark Automated slide stainer. The slides were then washed with dI $H_2O$ and incubated with 500 µl of 2.5 µg/ml hydrogen tetrabromoaurate (III) hydrate for 4 minutes at 37° C. The solution was rinsed with dI$H_2O$ and 250 µl of 50 mM $AgNO_3$ in 0.5 M Tris Buffer at pH 9.0 and 250 µl of 100 mM Ascorbic Acid Phosphate in a 0.5M DEA Buffer at pH 10.0 with 5% PVA (av. mol wt 70,000 to 100,000) was applied to each section. The slides were allowed to incubate for 10 minutes at 37° C. The slides were rinsed with dI $H_2O$. FIG. 11 demonstrates the signal without the amplification when compared to Example 8 (FIG. 10).

EXAMPLE 10

Synthesis of Hydroquinone-1,4-diphosphate

Hydroquinone was reacted with two equivalents of phosphorous oxychloride and two equivalents anhydrous pyridine in anhydrous toluene (to 0.1M) over 30 minutes. The mixture was refluxed for an additional 30 minutes and allowed to cool to ambient temperature. Pyridinium chloride was removed by filtration through a pad of diatomaceous earth and rinsed with a small volume of dry toluene. The filtrate was concentrated in vacuo at 40° C. and the residue hydrolyzed with aqueous ammonium carbonate to pH 7. The product was purified by reverse-phase separation on flash C18 silica gel to give the desired product as proven by MS, $^1$H and $^{13}$C-NMR.

EXAMPLE 11

Synthesis of Anthrahydroquinone-1,4-diphosphate and naphthohydroquinone-1,4-diphosphate The procedure of Example 10 is performed with the exception of using Anthrahydroquinone or naphthohydroquinone as the starting materials.

EXAMPLE 12

General Synthesis of Substrate Phosphates

Synthesis of Sesamol Phosphate $POCl_3$ (89.5 mmol) was transferred to a dry 500 ml round bottom flask under a nitrogen atmosphere. A solution of sesamol (35.8 mmol, 1 eq.) and triethylamine (71.7 mmol) in 200 mL of dry dichloromethane was added dropwise over four hours to the $POCl_3$ solution. After stirring at ambient temperature overnight, the solvent was removed by rotary evaporation. The residue was dissolved in 100 mL dichloromethane and the salts removed by filtering through Celite. The product was partitioned into water by quenching with 100 mL saturated ammonium carbonate. The organic layer was discarded and the aqueous phase was dried by rotary evaporation to give 8.2 grams (90% yield) of the desired phosphate. The product identity was confirmed by MS, and analysis by HPLC at 214 nm showed the product to be greater than 99% pure.

EXAMPLE 13

General Synthesis of Substrate Phosphates

Synthesis of Eugenol and PMCP Phosphates

The procedure of Example 12 is performed with the exception of using eugenol or PMCP (2,2,5,7,8-Pentamethyl-6-chromanol) as the starting materials.

EXAMPLE 14

Immunoblot ELISA of a Large Antigen with Antibody Adsorbed to a Membrane

Biodyne® A or B nylon 6,6 membrane from Pall Corporation is cut to 10×10 cm squares. These are subdivided into 1 cm segments by lines drawn with pencil and each square is numbered for identification. Serially diluted goat anti-rabbit IgG in PBS is added to the respective squares to give the final concentrations of 10 ng/μl, 100 ng/ng 1 μg/μl using 1 μl pipette. The samples are air dried and placed in Petri dishes containing PBS blocking buffer consisting of 0.5% casein (BDH Biochemicals, Ltd). The membranes are air dried again. 10 ml volumes of dilute antigen (rabbit anti-mouse IgG) of 1 μg/ml and 100 ng/ml in PBS is added to strips in Petri dishes and gently shaken for 30 minutes.

The liquid is decanted, replaced with 10 ml of wash solution consisting of 0.1% Triton X-100 (Bio-Rad Laboratories) and agitated for 5 minutes. The wash procedure is repeated twice. The final wash solution is replaced with 10 ml PBS. Petri dish is gently agitated for an additional 1 minute. The secondary goat anti-rabbit IgG-alkaline phosphatase conjugate is diluted 1:100 (v/v) in PBS and 10 ml of this conjugate solution is applied to the strips. The reaction is gently agitated for 60 minutes. The liquid is decanted, replaced with the wash solution consisting of 0.1% Triton X-100 (Bio-Rad Laboratories) and agitated for 5 minutes. The material is washed twice with deionized water and gently agitated for 1 minute. The squares are washed with 0.10 M solution of TRIS, pH 9. 5 μl of 0.05 M solution of ascorbate phosphate (Sigma) in TRIS buffer is added to each square followed by 5 μl of 0.05 M silver nitrate (Aldrich). The spot is dried and colloidal silver is developed with Silver Enhancer Kit (Product No. SE-100, Sigma, St. Louis, Mo.). The developed black precipitate of colloidal silver is read with a reflectometer or scanning densitometer.

EXAMPLE 15

ELISA of a Small Hapten (Drug) with Antibody Adsorbed to a Membrane

The analysis of illegal drugs may be performed using the present invention. Benzoylecgonine (BE) is a major metabolite of cocaine. It has a longer half-life in plasma and oral fluid than does the parent drug. Competitive ELISA employing the technology taught in the present invention may be employed as a screening test for cocaine abuse.

25 μl of an oral fluid specimen or calibrator is added to a microtiter plate well coated with anti-BE antibody. 100 μl of BE-alkaline phosphatase conjugate is added in TRIS buffer. Each microtiter plate is calibrated with 0, 10, 25, 50, and 100 μg/l calibrators. After 30 minutes of incubation, the plate is washed and 0.10 M solution of TRIS, pH 9. 5 μl of 0.05 M solution of ascorbate phosphate (Sigma) in TRIS buffer is added to each square followed by 5 μl of 0.05 M silver nitrate (Aldrich). The colloidal silver is developed with Silver Enhancer Kit (Sigma). The developed black precipitate of colloidal silver is read with a reflectometer or uv/vis plate reader. The transmittance is inversely proportional to the amount of deposited silver and directly proportional to the amount of the drug in the sample.

EXAMPLE 16

DNA Microarray Application

A nucleic acid microarray consisting of synthetic oligonucleotides or cDNA clones spotted on a modified glass microscope slide is hybridized to biotin labeled cDNA prepared from tumor tissue under conditions known in the art, such as, typically, a 37° C. exposure to a solution of 50% formamide in 2×SSC with 10% dextran sulfate and a blocking reagent such as bovine serum albumin (BSA) or partially hydrolysed casein. After washing, the slide is exposed to streptavidin-coupled alkaline phosphatase, the excess of which is subsequently removed by washing. The slide is washed with 0.10 M solution of TRIS, pH 9. A 50 μl aliquot of a 0.05 M solution of ascorbate phosphate (Sigma) in TRIS buffer is added to the slide followed by 50 μl of 0.05 M silver nitrate (Aldrich). The slide is rinsed in water and colloidal silver is developed with Silver Enhancer Kit (Sigma). The developed black precipitate of colloidal silver is recorded as a digital image which can be analyzed by computer. Alternatively, the slide can be directly analyzed using a reflectometer or scanning densitometer or by surface plasmon resonance.

It will be appreciated that the methods and compositions of the present invention are capable of being incorporated in the form of a variety of embodiments, only a few of which have been illustrated and described above. The invention may be embodied in other specific forms without departing from its spirit or essential characteristics. The described embodiments are to be considered in all respects only as illustrative and not restrictive. The scope of the invention is, therefore, indicated by the appended claims rather than the foregoing description. All changes which come within the meaning and range of equivalence of the claims are to be embraced within the scope of the invention.

All publications and patents mentioned in this specification are indicative of the level of skill of those skilled in the art to which this invention pertains. All publications and patents are herein incorporated by reference to the same extent as if each individual publication or patent application were specifically and individually indicated to be incorporated by reference.

What is claimed is:

1. A method of detecting and quantifying an analyte of interest from a biological sample in an enzyme immunoassay (EIA), comprising the steps of:
    (a) contacting said biological sample with a primary antibody immobilized on a solid support, such that a primary antibody-analyte complex will form when analyte is present in the biological sample;
    (b) contacting said complex formed in step (a) with a secondary antibody conjugated to a label enzyme selected from the group consisting of alkaline phosphatase, acid phosphatase, alpha- and beta-galactosidases, and esterases, such that a primary antibody-analyte-secondary antibody complex will form when analyte is present in the biological sample;

(c) contacting said primary antibody-analyte-secondary antibody complex formed in step (b) with a redox inactive reductive species in the presence of metal ion, wherein said redox inactive reductive species is a substrate for said label enzyme, and wherein said label enzyme converts said redox inactive reductive species to a redox active reductive species that reduces said metal ion such that a metal precipitate will form on the solid support following reduction of said metal ion;

(d) enhancing said metal precipitate; and (e) detecting and quantifying the analyte in the biological sample by quantifying the metal precipitate formed on the solid support.

2. The method of claim 1, wherein said label enzyme is alkaline phosphatase, and said redox-inactive reductive species is ascorbic acid phosphate.

3. The method of claim 1, wherein said label enzyme is alkaline phosphatase, and said redox-inactive reductive species is a hydroquinone phosphate derivative.

4. The method of claim 3, wherein said redox-inactive reductive species is hydroquinone diphosphate.

5. The method of claim 1, wherein said label enzyme is selected from the group consisting of alkaline phosphatase and acid phosphatase, and said redox-inactive reductive species is selected from the group consisting of hydroquinone mono- and di-phosphates, naphthohydroquinone mono- and di-phosphates, and anthrahydroquinone mono- and di-phosphates.

6. The method of claim 1, wherein said label enzyme is selected from the group consisting of alkaline phosphatase and acid phosphatase, and said redox-inactive reductive species is selected from the group consisting of sesamol phosphate, eugenol phosphate and alpha-tocopherol phosphate.

7. The method of claim 1, wherein said metal ion is selected from the group consisting of silver ion and gold ion.

8. The method of claim 7, wherein said metal ion is silver ion.

9. The method of claim 8, wherein prior to the reduction of silver ion in step (c), the biological sample is pretreated with gold ion.

10. The method of claim 1, wherein said EIA is an enzyme-linked immunosorbent assay (ELISA).

11. The method of claim 1, wherein said label enzyme is alkaline phosphatase.

12. The method of claim 1, wherein said label enzyme is acid phosphatase.

13. The method of claim 1, wherein said label enzyme is alpha- or beta-galactosidase.

14. The method of claim 1, wherein said label enzyme is an esterase.

* * * * *

UNITED STATES PATENT AND TRADEMARK OFFICE
CERTIFICATE OF CORRECTION

PATENT NO. : 7,642,064 B2 Page 1 of 1
APPLICATION NO. : 11/015646
DATED : January 5, 2010
INVENTOR(S) : Bieniarz et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1211 days.

Signed and Sealed this

Sixteenth Day of November, 2010

David J. Kappos
*Director of the United States Patent and Trademark Office*